US008580274B2

(12) United States Patent
Arakawa et al.

(10) Patent No.: US 8,580,274 B2
(45) Date of Patent: Nov. 12, 2013

(54) DRUG TRANSPORTER, AND ADJUVANT AND VACCINE EACH UTILIZING SAME

(75) Inventors: Takeshi Arakawa, Okinawa (JP); Takeshi Miyata, Okinawa (JP); Goro Matsuzaki, Okinawa (JP); Takafumi Tsuboi, Ehime (JP)

(73) Assignee: University of the Ryukyus, Nakagami-gun (JP)

( * ) Notice: Subject to any disclaimer, the term of this patent is extended or adjusted under 35 U.S.C. 154(b) by 0 days.

(21) Appl. No.: 13/148,832

(22) PCT Filed: Feb. 10, 2010

(86) PCT No.: PCT/JP2010/051915
§ 371 (c)(1),
(2), (4) Date: Nov. 18, 2011

(87) PCT Pub. No.: WO2010/092963
PCT Pub. Date: Aug. 19, 2010

(65) Prior Publication Data
US 2012/0100165 A1   Apr. 26, 2012

(30) Foreign Application Priority Data

Feb. 10, 2009   (JP) ................. 2009-028134

(51) Int. Cl.
*A61K 39/385*   (2006.01)
*A61K 39/00*   (2006.01)
*A61K 39/395*   (2006.01)
*C12P 21/08*   (2006.01)

(52) U.S. Cl.
USPC ............. 424/193.1; 424/134.1; 424/144.1; 424/184.1; 424/185.1; 530/387.3

(58) Field of Classification Search
None
See application file for complete search history.

(56) References Cited

U.S. PATENT DOCUMENTS

| 5,411,732 A | 5/1995 | Lowenadler et al. |
| 2005/0137156 A1 | 6/2005 | Johnston et al. |
| 2005/0170337 A1 | 8/2005 | Hogle et al. |
| 2007/0104726 A1* | 5/2007 | Andreoletti et al. ....... 424/189.1 |
| 2007/0160628 A1 | 7/2007 | Birkett et al. |
| 2007/0172504 A1 | 7/2007 | Shirwan et al. |
| 2009/0028884 A1* | 1/2009 | Schwabe ................... 424/178.1 |

FOREIGN PATENT DOCUMENTS

| JP | 62 272989 | 11/1987 |
| JP | 2006 505252 | 2/2006 |
| JP | 2006 519781 | 8/2006 |
| JP | 2007 528210 | 10/2007 |
| JP | 2008 514585 | 5/2008 |
| JP | 2008 536916 | 9/2008 |
| WO | WO 99/63333 * | 9/1999 |
| WO | WO 2005/077976 A2 | 8/2005 |
| WO | 2006 078567 | 7/2006 |
| WO | 2007 027640 | 3/2007 |
| WO | 2007 067681 | 6/2007 |
| WO | 2008 068017 | 6/2008 |
| WO | 2009 109428 | 9/2009 |

OTHER PUBLICATIONS

Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Eriksson et al. 2003. Vaccine 22:185-193).*
Saini et al. 2003. Journal of Virology 77:3487-3494.*
Belitskaya, S. Y. et al., "Design of Chimeric Proteins on the Basis of a Pentameric Superhelical Fragment of Human Cartilage Oligomeric Matrix Protein: I. The Properties of a Hybrid Containing the Immunodominant Domain of the Circumsporozoite Protein of Plasmodium Falciparum", Russian Journal of Bioorganic Chemistry, vol. 30, No. 1, pp. 35-41, (2004).
Belitskaya, S. Y. et al., "Design of Chmeric Proteins on the Basis of a Pentameric Superhelical Fragment of Human Cartilage Oligomeric Matrix Protein: II.[1] The Properties of a Hybrid Containing the Antigen VNTR (MUC1) from Human Tumors", Russian Journal of Bioorganic Chemistry, vol. 30, No. 1, pp. 42-46, (2004).
Dempsey, P. W. et al., "C3d of Complement as a Molecular Adjuvant: Bridging Innate and Acquired Immunity", Science, vol. 271, pp. 348-350, (Jan. 19, 1996).
Lupas, A. N. et al., "The Structure of α-Helical Coiled Coils", Advances in Protein Chemistry, vol. 70, pp. 37-78, (2005).
Peters, J. et al., "Tetrabrachion: A Filamentous Archaebacterial Surface Protein Assembly of Unusual Structure and Extreme Stability", J. Mol. Biol., vol. 245, pp. 385-401, (1995).
Wikstrom, M. et al., "Three-Dimensional Solution Structure of an Immunoglobulin Light Chain-Binding Domain of Protein L. Comparison with the IgG-Binding Domains of Protein G", Biochemistry, vol. 33, pp. 14011-14017, (1994).
Blom, A. M. et al., "Complement Inhibitor C4b-Binding Protein-Friend or Foe in the Innate Immune System?", Molecular Immunology, vol. 40, pp. 1333-1346, (2004).
Sakane, I. et al., "Mechanical Unfolding of Covalently Linked GroES: Evidence of Structural Subunit Intermediates", Protein Science, vol. 18, pp. 252-257, (2009).
Leadbetter, E. A. et al., "NK T Cells Provide Lipid Antigen-Specific Cognate Help for B Cells", PNAS, vol. 105, No. 24, pp. 8339-8344, (Jun. 17, 2008).
Mitchison, N. A., "T-Cell-B-Cell Cooperation", Nature Reviews, Immunology, vol. 4, pp. 308-312, (Apr. 2004).

(Continued)

Primary Examiner — Shulamith H Shafer
(74) Attorney, Agent, or Firm — Oblon, Spivak, McClelland, Maier & Neustadt, L.L.P.

(57) ABSTRACT

An objective of the invention is to provide a drug delivery vehicle capable of allowing a vaccine or adjuvant to reach a target cell or tissue efficiently while being capable of improving the immunogenicity of the vaccine or capable of enhancing the immunostimulating effect of the adjuvant as well as a vaccine or adjuvant utilizing the same. Said drug delivery vehicle contains a multimeric protein having a coiled coil structure and a ligand molecule to a receptor of an immune cell.

13 Claims, 3 Drawing Sheets

(56) References Cited

OTHER PUBLICATIONS

Roosnek, E. et al., "Efficient and Selective Presentation of Antigen-Antibody Complexes by Rheumatoid Factor B Cells", J.Exp. Med., vol. 173, pp. 487-489, (Feb. 1991).

International Search Report Issued Mar. 16, 2010 in PCT/JP10/051915 filed Feb. 10, 2010.

International Preliminary Report on Patentability Issued on Apr. 13, 2011 in PCT/JP10/051915 filed Feb. 10, 2010.

Extended European Search Report issued Aug. 7, 2012 in Patent Application No. 10741240.5.

Ulrich Schroeder, et al., "Peptide Nanoparticles Serve as a Powerful Platform for the Immunogenic Display of Poorly Antigenic Actin Determinants", Journal of Molecular Biology, vol. 386, No. 5, XP002679824A, Mar. 13, 2009, pp. 1368-1381.

Takeshi Miyata, et al., "Tricomponent Immunopotentiating System as a Novel Molecular Design Strategy for Malaria Vaccine Development", Infection and Immunity, vol. 79, No. 10, XP002679825A, Oct. 2011, pp. 4260-4275.

* cited by examiner

A number in the graph indicates a % infection prevention when compared with the non-immunized group.

SEQUENCE LISTING

<160> NUMBER OF SEQ ID NOS: 41

<210> SEQ ID NO 1
<211> LENGTH: 755
<212> TYPE: PRT
<213> ORGANISM: Unknown
<220> FEATURE:
<223> OTHER INFORMATION: Description of Unknown: Mammalian
      polypeptide

<400> SEQUENCE: 1

Met Ser Pro Thr Ala Cys Val Leu Val Leu Ala Leu Ala Ala Leu Arg
1               5                   10                  15

Ala Thr Gly Gln Gly Gln Ile Pro Leu Gly Gly Asp Leu Ala Pro Gln
            20                  25                  30

Met Leu Arg Glu Leu Gln Glu Thr Asn Ala Ala Leu Gln Asp Val Arg
        35                  40                  45

Glu Leu Leu Arg His Arg Val Lys Glu Ile Thr Phe Leu Lys Asn Thr
    50                  55                  60

Val Met Glu Cys Asp Ala Cys Gly Met Gln Pro Ala Arg Thr Pro Gly
65                  70                  75                  80

Leu Ser Val Arg Pro Val Ala Leu Cys Ala Pro Gly Ser Cys Phe Pro
                85                  90                  95

Gly Val Val Cys Thr Glu Thr Ala Thr Gly Ala Arg Cys Gly Pro Cys
            100                 105                 110

Pro Pro Gly Tyr Thr Gly Asn Gly Ser His Cys Thr Asp Val Asn Glu
        115                 120                 125

Cys Asn Ala His Pro Cys Phe Pro Arg Val Arg Cys Ile Asn Thr Ser
    130                 135                 140

Pro Gly Phe His Cys Glu Ala Cys Pro Pro Gly Phe Ser Gly Pro Thr
145                 150                 155                 160

His Glu Gly Val Gly Leu Thr Phe Ala Lys Thr Asn Lys Gln Val Cys
                165                 170                 175

Thr Asp Ile Asn Glu Cys Glu Thr Gly Gln His Asn Cys Val Pro Asn
            180                 185                 190

Ser Val Cys Val Asn Thr Arg Gly Ser Phe Gln Cys Gly Pro Cys Gln
        195                 200                 205

Pro Gly Phe Val Gly Asp Gln Arg Ser Gly Cys Gln Arg Arg Gly Gln
    210                 215                 220

His Phe Cys Pro Asp Gly Ser Pro Ser Pro Cys His Glu Lys Ala Asp
225                 230                 235                 240

Cys Ile Leu Glu Arg Asp Gly Ser Arg Ser Cys Val Cys Ala Val Gly
                245                 250                 255

Trp Ala Gly Asn Gly Leu Leu Cys Gly Arg Asp Thr Asp Leu Asp Gly
            260                 265                 270

Phe Pro Asp Glu Lys Leu Arg Cys Ser Glu Arg Gln Cys Arg Lys Asp
        275                 280                 285

Asn Cys Val Thr Val Pro Asn Ser Gly Gln Glu Asp Val Asp Arg Asp
    290                 295                 300

Arg Ile Gly Asp Ala Cys Asp Pro Asp Ala Asp Gly Asp Gly Val Pro
305                 310                 315                 320

Asn Glu Gln Asp Asn Cys Pro Leu Val Arg Asn Pro Asp Gln Arg Asn
                325                 330                 335

Ser Asp Lys Asp Lys Trp Gly Asp Ala Cys Asp Asn Cys Arg Ser Gln
            340                 345                 350

```
Lys Asn Asp Asp Gln Lys Asp Thr Asp Arg Asp Gly Gln Gly Asp Ala
            355                 360                 365
Cys Asp Asp Ile Asp Gly Asp Arg Ile Arg Asn Val Ala Asp Asn
            370                 375                 380
Cys Pro Arg Val Pro Asn Phe Asp Gln Ser Asp Ser Asp Gly Asp Gly
385                 390                 395                 400
Val Gly Asp Ala Cys Asp Asn Cys Pro Gln Lys Asp Asn Pro Asp Gln
                405                 410                 415
Arg Asp Val Asp His Asp Phe Val Gly Asp Ala Cys Asp Ser Asp Gln
            420                 425                 430
Asp Gln Asp Gly Asp Gly His Gln Asp Ser Arg Asp Asn Cys Pro Thr
            435                 440                 445
Val Pro Asn Ser Ala Gln Gln Asp Ser Asp His Asp Gly Lys Gly Asp
            450                 455                 460
Ala Cys Asp Asp Asp Asp Asn Asp Gly Val Pro Asp Ser Arg Asp
465                 470                 475                 480
Asn Cys Arg Leu Val Pro Asn Pro Gly Gln Glu Asp Asn Asp Arg Asp
                485                 490                 495
Gly Val Gly Asp Ala Cys Gln Gly Asp Phe Asp Ala Asp Lys Val Ile
            500                 505                 510
Asp Lys Ile Asp Val Cys Pro Glu Asn Ala Glu Val Thr Leu Thr Asp
            515                 520                 525
Phe Arg Ala Phe Gln Thr Val Val Leu Asp Pro Glu Gly Asp Ala Gln
            530                 535                 540
Ile Asp Pro Asn Trp Val Val Leu Asn Gln Gly Met Glu Ile Val Gln
545                 550                 555                 560
Thr Met Asn Ser Asp Pro Gly Leu Ala Val Gly Tyr Thr Ala Phe Asn
                565                 570                 575
Gly Val Asp Phe Glu Gly Thr Phe His Val Asn Thr Ala Thr Asp Asp
            580                 585                 590
Asp Tyr Ala Gly Phe Ile Phe Gly Tyr Gln Asp Ser Ser Ser Phe Tyr
            595                 600                 605
Val Val Met Trp Lys Gln Met Glu Gln Thr Tyr Trp Gln Ala Asn Pro
            610                 615                 620
Phe Arg Ala Val Ala Glu Pro Gly Ile Gln Leu Lys Ala Val Lys Ser
625                 630                 635                 640
Ser Thr Gly Pro Gly Glu Gln Leu Arg Asn Ala Leu Trp His Thr Gly
                645                 650                 655
Asp Thr Ala Ser Gln Val Arg Leu Leu Trp Lys Asp Pro Arg Asn Val
            660                 665                 670
Gly Trp Lys Asp Lys Thr Ser Tyr Arg Trp Phe Leu Gln His Arg Pro
            675                 680                 685
Gln Val Gly Tyr Ile Arg Val Arg Phe Tyr Glu Gly Pro Glu Leu Val
            690                 695                 700
Ala Asp Ser Asn Val Val Leu Asp Thr Ala Met Arg Gly Gly Arg Leu
705                 710                 715                 720
Gly Val Phe Cys Phe Ser Gln Glu Asn Ile Ile Trp Ala Asn Leu Arg
                725                 730                 735
Tyr Arg Cys Asn Asp Thr Ile Pro Glu Asp Tyr Glu Arg His Arg Leu
                740                 745                 750
Arg Arg Ala
            755
```

```
<210> SEQ ID NO 2
<211> LENGTH: 1524
<212> TYPE: PRT
<213> ORGANISM: Staphylothermus marinus

<400> SEQUENCE: 2

Met Asn Arg Val Leu Ala Tyr Ser Leu Leu Ala Ile Met Thr Leu Ser
1               5                   10                  15

Leu Leu Ile Ile Pro Ala Pro Gly Ile Ala Gln Arg Ile Thr Val Gly
            20                  25                  30

Val Ser Val Lys Ala Gly Thr Tyr Asn Phe Tyr Asn Ile Thr Pro Thr
        35                  40                  45

Thr Gln Thr Val Glu Val Thr Asp Asn Gly Met Leu Arg Val Ile Ile
    50                  55                  60

Asn Arg Thr Glu Ala Thr Glu Leu Gly Thr Thr Ile Arg Leu Ala Phe
65                  70                  75                  80

Ile Leu Asp Thr Asp Lys Tyr Asp Pro Asn Val Gly Gly Tyr Phe Leu
                85                  90                  95

Asn Val Ser Asn Ile Gly Val Tyr Ala Pro Ser Asp Pro Thr Gln Ser
            100                 105                 110

Pro Tyr Gly Gly Val Ile Asp Ile Thr Gln Asn Ser Thr Leu Thr Asp
        115                 120                 125

Gly Thr Gln Val Val Gly Asn Val Thr Val Asn Gly Gly Asn Asn
    130                 135                 140

Val Ile Ile Leu Ile Asp Leu Ser Lys Leu Pro Asp Leu Gln Asn Val
145                 150                 155                 160

Val Tyr Ile Thr Asn Val Tyr Thr Glu Thr Ser Thr Ala Asn Leu
                165                 170                 175

Thr Asn Thr Leu Leu Arg Val Lys Ala Phe Asp Ala Ala Ser Trp Asp
            180                 185                 190

Ala Val Ile Ser Gly Asn Gln Phe Lys Ile Leu Tyr Ile Pro Ser Leu
        195                 200                 205

Cys Lys Tyr Val Lys Ile Asn Val Ile His Ser Pro Ala Ile Val Gly
    210                 215                 220

Thr Asn Val Asp Val Ile Val Ser Phe His Lys Tyr Phe Ser Leu Val
225                 230                 235                 240

Gln Ser Ile Ala Gly Val Ser Leu Asp Ile Thr Val Asp Asn Lys Thr
                245                 250                 255

Gln Leu Asn Met Thr Asn Tyr Tyr Asn Ala Thr Glu Asn Tyr Val Leu
            260                 265                 270

Ala Thr Phe Ile Asn Gly Asn Leu Thr Val Gly Gly Ser Glu Val Phe
        275                 280                 285

Ser Ser Pro Thr Val Thr Val Ile Asn Ala Ser Thr Phe Lys Tyr Ser
    290                 295                 300

Gly Gln Val Lys Asp Tyr Ala Pro Thr Val Ala Asp Thr Ala Thr Pro
305                 310                 315                 320

Trp Val Arg Thr Leu Asn Lys Phe Glu Val Glu Phe Arg His Glu Ile
                325                 330                 335

Val Asn Glu Thr His Asp Leu Ile Phe Tyr Ile His Cys Asp Ser Asp
            340                 345                 350

Thr Val Ser Tyr Asp Thr Trp Pro Phe Leu Ile Val Asn Ala Ser Leu
        355                 360                 365

Asp Ile Thr Thr Thr Glu Val Ala Phe Asn Ser Thr Thr Ile Asn Pro
    370                 375                 380

Gly Asp Ile Val Asn Phe Thr Ala His Asn Val Pro Leu Gln Tyr Leu
```

-continued

```
            385                 390                 395                 400
Thr Ala Thr Asn Tyr Gly Val Leu Arg Phe Gln Leu Ile Asn Pro Ala
                    405                 410                 415
Leu Val Val Tyr Val Pro Val Ser Asn Met Thr Leu Ser Ala Asn Thr
                    420                 425                 430
Thr Thr Gly Ile Ile Asn Gly Ser Phe Val Leu Pro Asp Ala Pro Tyr
                    435                 440                 445
Gly Gly Leu Asp Tyr Leu Thr Tyr Leu Val Phe Asn Asp Gly Lys Phe
                    450                 455                 460
Ile Ala Asn Gly Tyr Ile Thr Val Ser Pro Cys Ile Glu Thr Tyr Val
465                 470                 475                 480
Leu Thr Asn Thr Ser Ala Tyr Ala Glu Asp Ala Gly Ser Ser Tyr Ile
                    485                 490                 495
Gly Arg Phe Val Pro Gly Tyr Thr Ser Val Pro Gly Asp Tyr Ile Val
                    500                 505                 510
Ile Lys Gly Tyr Gly Phe Ala Leu Ser Asn Leu Thr Gly Phe Thr Val
                    515                 520                 525
Ser Ile Asn Asn Thr Asp Val Ile Ile Leu Asn Ala Thr Tyr Asn Ala
530                 535                 540
Ser Thr Gly Lys Ile Ile Ile Leu Ala Lys Leu Leu Asp Thr Asn Gly
545                 550                 555                 560
Thr Pro Ile Pro Val Gly Ala Gly Phe Ile Arg Val Gly Gln Asn Gly
                    565                 570                 575
Thr Thr Asn Ile Ala Tyr Ala Pro Phe Asn Val Thr Arg Asn Ser Gly
                    580                 585                 590
Leu Glu Lys Val Leu Phe Asn Pro Arg Trp Phe Tyr Asn Gly Thr Tyr
                    595                 600                 605
Tyr Ile Glu His Asp Lys Leu Gly Asp Pro Tyr Leu Tyr Phe Pro Val
                    610                 615                 620
Asp Tyr Pro Leu Val Asn Asn Thr Phe Thr Thr Glu Met Trp Pro Phe
625                 630                 635                 640
Asn Thr Thr Ile Glu Val Ile Gly Trp Pro Thr Asn Thr Phe Thr Leu
                    645                 650                 655
Lys Ala Phe Asn Lys Glu Phe Asn Leu Ser Phe Asn Leu Leu Thr Leu
                    660                 665                 670
Ser Leu Thr Asn Gly Tyr Asn Met Thr Asn Leu Tyr Asn Leu Thr Ile
                    675                 680                 685
Pro Phe Leu Pro Tyr Gly Asn Tyr Thr Leu Leu Glu Gly Thr Leu Leu
                    690                 695                 700
Ser Val Asn Asn Arg Thr Val Phe Thr Val His Met Gly Ile Asn Val
705                 710                 715                 720
Asp Leu Asp Ser Cys Gly Asn Gly Thr Leu Ser Ile Thr Val Val Gly
                    725                 730                 735
Ala Ala Pro Asn Thr Glu Tyr Asn Phe Thr Phe Gly Tyr Gln Val His
                    740                 745                 750
Asp Leu Asn Tyr Gly Ile Thr Arg Tyr Ile Ser Pro Gln Trp Asn Gly
                    755                 760                 765
Thr Trp Asn Ile Ser Leu Val Thr Asp Ile Tyr Gly Thr Gly Ser Thr
                    770                 775                 780
Ser Val Pro Leu Ile Thr Leu Tyr Pro Thr Ser Tyr Val Ile Asn Ala
785                 790                 795                 800
Thr Trp Asp Val Ile Thr Trp Leu Arg Leu Ser Gly Ser Gly Thr Leu
                    805                 810                 815
```

-continued

Asp Leu Leu Phe Ser Val Asp Val Ser Tyr Asn Gly Phe Thr Asp Asn
                820                 825                 830

Leu Thr Thr Pro Ile Thr Tyr Val Phe Gly Pro Ser Asp Thr Thr Pro
            835                 840                 845

Gly Ser Phe Asn Ile Tyr Val Asn Thr Thr Tyr Asn Val Ser Val Val
        850                 855                 860

Arg Val Ala Val Asp Tyr Leu Pro Arg Thr Asn Val Val Ile Ser Val
865                 870                 875                 880

Pro Glu Thr Val Leu Pro Gly Asp Thr Ile Thr Val Gln Ile Phe Pro
                885                 890                 895

His His Asn Glu Val Trp Gly Phe Ile Glu Pro Thr Ala Leu Phe Asp
            900                 905                 910

Glu Asn Gln Leu Leu Gly Trp Tyr Leu Thr Val Arg Leu Val Asp Pro
        915                 920                 925

Leu Ser Asn Thr Val Val Glu Arg Val Ala Gly Tyr Tyr Ala Gly Asn
    930                 935                 940

Leu Ile Val Glu Asp Val Asp Gly Asp Gly Asp Asn Glu Val Trp Phe
945                 950                 955                 960

Val Val Asn Leu Thr Ala Pro Leu Val Leu Gly Val Asp Lys Thr Tyr
                965                 970                 975

Arg Val Asp Val Glu Leu Phe Leu Ala Val Leu Asn Pro Ser Ser Asn
            980                 985                 990

Ile Thr Gly Val Thr Ala Val Asp Asn Glu Cys Tyr Val Gln Leu Asp
        995                 1000                1005

Leu Asn Gly Thr Ile Tyr Trp Asn Gly Leu Gly Ser Gly Ile Met
    1010                1015                1020

Leu Gly Gly Asp Gly Gln Ile Val Thr Val Leu Gly Val Leu Glu
    1025                1030                1035

Gly Lys Leu Asp Thr Ile Lys Asp Gly Ile Ala Glu Ile Asn Ala
    1040                1045                1050

Thr Val Asn Asp Ile Asn Thr Tyr Leu Lys Val Asn Val Thr Asp
    1055                1060                1065

Leu Leu Lys Thr Ile Asn Asn Ser Val Val Met Ile Lys Asn Asp
    1070                1075                1080

Thr Ala Thr Leu Ile Ile Gly Gln Ala Glu Ile Lys Ala Lys Leu
    1085                1090                1095

Asp Asp Leu Leu Asn Leu Thr Ser Gln Val Asn Asp Thr Val Thr
    1100                1105                1110

Met Ile Leu Ala Cys Cys Asn Asn Ala Ser Lys Val Leu Asn Arg
    1115                1120                1125

Met Glu Gly Thr Leu Asn Ser Thr Tyr Thr Gly Val Leu Asn Val
    1130                1135                1140

Lys Ser Asp Leu Ser Thr Leu Ile Asp Thr Val Asn Asn Val Val
    1145                1150                1155

Ile Pro Lys Phe Asn Glu Leu Tyr Asp Asn Val Thr Val Glu Ile
    1160                1165                1170

Asn Ala Ser Arg Asp Leu Ile Ile Gln Lys Ile Ser Ser Val Asn
    1175                1180                1185

Asp Ser Leu Thr Thr Ile Ile Ser Ala Gly Phe Asn Asp Val Glu
    1190                1195                1200

Ala Met Ile Ser Asn Leu Asn Thr Thr Leu Leu Asn Arg Ile Asp
    1205                1210                1215

Glu Leu Glu Gly Thr Leu Leu Phe Tyr Met Thr Ala Asn Glu Gln
    1220                1225                1230

```
Arg Leu Phe Gly Ile Ile Asn Glu Thr Ala Asp Asp Ile Val Tyr
    1235                1240                1245

Arg Leu Thr Val Ile Ile Asp Asp Arg Tyr Glu Ser Leu Lys Asn
    1250                1255                1260

Leu Ile Thr Leu Arg Ala Asp Arg Leu Glu Met Ile Ile Asn Asp
    1265                1270                1275

Asn Val Ser Thr Ile Leu Ala Ser Ile Gly Asn Val Asn Leu Thr
    1280                1285                1290

Val Phe Asn Lys Leu Asn Asp Leu Glu Ile Glu Leu Gly Asp Val
    1295                1300                1305

Asn Ala Thr Ile Asn Ala Gly Ile Phe Gln Ile Gln Ser Asn Leu
    1310                1315                1320

Gly Asn Ala Asn Gln Leu Ile Leu Asp Thr Leu Thr Ser Ser Lys
    1325                1330                1335

Val Glu Ile Leu Asn Ala Ile Ser Ser Asn Ala Ser Ala Ile Ser
    1340                1345                1350

Ser Glu Ile His Asn Ala Val Asn Gln Leu Ser Thr Leu Val Leu
    1355                1360                1365

Gln Val Asn Asp Thr Leu Thr Leu Lys Ile Thr Gly Glu Ala Asp
    1370                1375                1380

Asn Ile Leu Asn Phe Leu Ser Ser Leu Glu Gly Ser Met Asn Thr
    1385                1390                1395

Gly Phe Asn Asn Val Thr Ser Thr Leu Ser Ala Val Glu Asn Asn
    1400                1405                1410

Ile Leu Gly Lys Ile Thr Asp Thr Ser Asn Leu Leu Ser Ser Lys
    1415                1420                1425

Ile Asp Asn Thr Leu Ser Thr Leu Gln Asp Leu Ile Thr Ser Thr
    1430                1435                1440

Ser Asn Asp Leu Lys Asn Ser Ile Ser Ser Ala Lys Asn Asp Ile
    1445                1450                1455

Val Ser Ser Leu Ser Ser Lys Val Asp Ser Ser Thr Gln Thr Leu
    1460                1465                1470

Ser Thr Lys Leu Asp Asp Leu Lys Ser Ala Gln Glu Ser Asn Thr
    1475                1480                1485

Asn Ser Ile Asn Asn Asn Ile Met Leu Phe Gly Ala Ala Ser Leu
    1490                1495                1500

Ile Leu Leu Ile Val Thr Ile Gly Leu Val Gly Tyr Arg Leu Ile
    1505                1510                1515

Ala Arg Arg Arg Val Gly
    1520

<210> SEQ ID NO 3
<211> LENGTH: 455
<212> TYPE: PRT
<213> ORGANISM: Reovirus sp.

<400> SEQUENCE: 3

Met Asp Pro Arg Leu Arg Glu Glu Val Val Arg Leu Ile Ile Ala Leu
1               5                   10                  15

Thr Ser Asp Asn Gly Ala Ser Leu Ser Lys Gly Leu Glu Ser Arg Val
                20                  25                  30

Ser Ala Leu Glu Lys Thr Ser Gln Ile His Ser Asp Thr Ile Leu Arg
            35                  40                  45

Ile Thr Gln Gly Leu Asp Asp Ala Asn Lys Arg Ile Ile Ala Leu Glu
        50                  55                  60
```

```
Gln Ser Arg Asp Asp Leu Val Ala Ser Val Ser Asp Ala Gln Leu Ala
 65                  70                  75                  80

Ile Ser Arg Leu Glu Ser Ser Ile Gly Ala Leu Gln Thr Val Val Asn
                 85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160

Arg Ile Thr Thr Leu Glu Arg Thr Ala Val Thr Ser Ala Gly Ala Pro
                165                 170                 175

Leu Ser Ile Arg Asn Asn Arg Met Thr Met Gly Leu Asn Asp Gly Leu
            180                 185                 190

Thr Leu Ser Gly Asn Asn Leu Ala Ile Arg Leu Pro Gly Asn Thr Gly
        195                 200                 205

Leu Asn Ile Gln Asn Gly Gly Leu Gln Phe Arg Phe Asn Thr Asp Gln
    210                 215                 220

Phe Gln Ile Val Asn Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
        355                 360                 365

Asn Phe Val Thr Gly Leu Leu Pro Pro Leu Leu Thr Gly Asp Thr Glu
370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
        435                 440                 445

Ser Tyr Pro Arg Ser Phe Thr
    450                 455

<210> SEQ ID NO 4
<211> LENGTH: 214
<212> TYPE: PRT
```

-continued

<213> ORGANISM: Hepatitis delta virus

<400> SEQUENCE: 4

```
Met Ser Arg Ser Glu Arg Arg Lys Asp Arg Gly Gly Arg Glu Asp Ile
1               5                   10                  15

Leu Glu Gln Trp Val Ser Gly Arg Lys Lys Leu Glu Glu Leu Glu Arg
            20                  25                  30

Asp Leu Arg Lys Leu Lys Lys Lys Ile Lys Lys Leu Glu Glu Asp Asn
        35                  40                  45

Pro Trp Leu Gly Asn Ile Lys Gly Ile Ile Gly Lys Lys Asp Lys Asp
    50                  55                  60

Gly Glu Gly Ala Pro Pro Ala Lys Lys Leu Arg Met Asp Gln Met Glu
65                  70                  75                  80

Ile Asp Ala Gly Pro Arg Lys Arg Pro Leu Arg Gly Gly Phe Thr Asp
                85                  90                  95

Lys Glu Arg Gln Asp His Arg Arg Arg Lys Ala Leu Glu Asn Lys Arg
            100                 105                 110

Lys Gln Leu Ser Ser Gly Gly Lys Ser Leu Ser Arg Glu Glu Glu Glu
        115                 120                 125

Glu Leu Lys Arg Leu Thr Glu Glu Asp Glu Lys Arg Glu Arg Arg Ile
130                 135                 140

Ala Gly Pro Ser Val Gly Gly Val Asn Pro Leu Glu Gly Gly Ser Arg
145                 150                 155                 160

Gly Ala Pro Gly Gly Gly Phe Val Pro Ser Met Gln Gly Val Pro Glu
                165                 170                 175

Ser Pro Phe Ala Arg Thr Gly Glu Gly Leu Asp Ile Arg Gly Ser Gln
            180                 185                 190

Gly Phe Pro Trp Asp Ile Leu Phe Pro Ala Asp Pro Pro Phe Ser Pro
        195                 200                 205

Gln Ser Cys Arg Pro Gln
    210
```

<210> SEQ ID NO 5
<211> LENGTH: 55
<212> TYPE: PRT
<213> ORGANISM: Unknown
<220> FEATURE:
<223> OTHER INFORMATION: Description of Unknown: Mammalian
      polypeptide

<400> SEQUENCE: 5

```
Gly Gly Asp Leu Ala Pro Gln Met Leu Arg Glu Leu Gln Glu Thr Asn
1               5                   10                  15

Ala Ala Leu Gln Asp Val Arg Glu Leu Leu Arg Gln Gly Val Lys Glu
            20                  25                  30

Ile Thr Phe Leu Lys Asn Thr Val Met Glu Cys Asp Ala Cys Gly Met
        35                  40                  45

Gln Pro Ala Arg Thr Pro Gly
    50                  55
```

<210> SEQ ID NO 6
<211> LENGTH: 46
<212> TYPE: PRT
<213> ORGANISM: Unknown
<220> FEATURE:
<223> OTHER INFORMATION: Description of Unknown: Mammalian
      polypeptide

<400> SEQUENCE: 6

```
Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Val Lys Glu Ile
                20                  25                  30

Thr Phe Leu Lys Asn Thr Val Met Glu Cys Asp Ala Cys Gly
            35                  40                  45

<210> SEQ ID NO 7
<211> LENGTH: 58
<212> TYPE: PRT
<213> ORGANISM: Staphylococcus sp.

<400> SEQUENCE: 7

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
                20                  25                  30

Ser Leu Lys Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 8
<211> LENGTH: 59
<212> TYPE: PRT
<213> ORGANISM: Streptococcus sp.

<400> SEQUENCE: 8

Pro Ala Val Thr Thr Tyr Lys Leu Val Ile Asn Gly Lys Thr Leu Lys
1               5                   10                  15

Gly Glu Thr Thr Thr Glu Ala Val Asp Ala Ala Thr Ala Glu Lys Val
                20                  25                  30

Phe Lys Gln Tyr Ala Asn Asp Asn Gly Val Asp Gly Glu Trp Thr Tyr
            35                  40                  45

Asp Asp Ala Thr Lys Thr Phe Thr Val Thr Glu
        50                  55

<210> SEQ ID NO 9
<211> LENGTH: 992
<212> TYPE: PRT
<213> ORGANISM: Peptostreptococcus magnus

<400> SEQUENCE: 9

Met Lys Ile Asn Lys Lys Leu Leu Met Ala Ala Leu Ala Gly Ala Ile
1               5                   10                  15

Val Val Gly Gly Gly Ala Asn Ala Tyr Ala Ala Glu Glu Asp Asn Thr
                20                  25                  30

Asp Asn Asn Leu Ser Met Asp Glu Ile Ser Asp Ala Tyr Phe Asp Tyr
            35                  40                  45

His Gly Asp Val Ser Asp Ser Val Asp Pro Val Glu Glu Ile Asp
    50                  55                  60

Glu Ala Leu Ala Lys Ala Leu Ala Glu Ala Lys Glu Thr Ala Lys Lys
65                  70                  75                  80

His Ile Asp Ser Leu Asn His Leu Ser Glu Thr Ala Lys Lys Leu Ala
                85                  90                  95

Lys Asn Asp Ile Asp Ser Ala Thr Thr Ile Asn Ala Ile Asn Asp Ile
            100                 105                 110

Val Ala Arg Ala Asp Val Met Glu Arg Lys Thr Ala Glu Lys Glu Glu
        115                 120                 125
```

-continued

```
Ala Glu Lys Leu Ala Ala Lys Glu Thr Ala Lys Lys His Ile Asp
    130                 135                 140

Glu Leu Lys His Leu Ala Asp Lys Thr Lys Glu Leu Ala Lys Arg Asp
145                 150                 155                 160

Ile Asp Ser Ala Thr Thr Ile Asn Ala Ile Asn Asp Ile Val Ala Arg
                165                 170                 175

Ala Asp Val Met Glu Arg Lys Thr Ala Glu Lys Glu Ala Glu Lys
            180                 185                 190

Leu Ala Ala Ala Lys Glu Thr Ala Lys Lys His Ile Asp Glu Leu Lys
            195                 200                 205

His Leu Ala Asp Lys Thr Lys Glu Leu Ala Lys Arg Asp Ile Asp Ser
    210                 215                 220

Ala Thr Thr Ile Asp Ala Ile Asn Asp Ile Val Ala Arg Ala Asp Val
225                 230                 235                 240

Met Glu Arg Lys Leu Ser Glu Lys Glu Thr Pro Glu Pro Glu Glu Glu
                245                 250                 255

Val Thr Ile Lys Ala Asn Leu Ile Phe Ala Asp Gly Ser Thr Gln Asn
            260                 265                 270

Ala Glu Phe Lys Gly Thr Phe Ala Lys Ala Val Ser Asp Ala Tyr Ala
    275                 280                 285

Tyr Ala Asp Ala Leu Lys Lys Asp Asn Gly Glu Tyr Thr Val Asp Val
    290                 295                 300

Ala Asp Lys Gly Leu Thr Leu Asn Ile Lys Phe Ala Gly Lys Lys Glu
305                 310                 315                 320

Lys Pro Glu Glu Pro Lys Glu Val Thr Ile Lys Val Asn Leu Ile
                325                 330                 335

Phe Ala Asp Gly Lys Thr Gln Thr Ala Glu Phe Lys Gly Thr Phe Glu
                340                 345                 350

Glu Ala Thr Ala Lys Ala Tyr Ala Tyr Ala Asp Leu Leu Ala Lys Glu
            355                 360                 365

Asn Gly Glu Tyr Thr Ala Asp Leu Glu Asp Gly Gly Asn Thr Ile Asn
    370                 375                 380

Ile Lys Phe Ala Gly Lys Glu Thr Pro Glu Thr Pro Glu Glu Pro Lys
385                 390                 395                 400

Glu Glu Val Thr Ile Lys Val Asn Leu Ile Phe Ala Asp Gly Lys Ile
                405                 410                 415

Gln Thr Ala Glu Phe Lys Gly Thr Phe Glu Glu Ala Thr Ala Lys Ala
            420                 425                 430

Tyr Ala Tyr Ala Asn Leu Leu Ala Lys Glu Asn Gly Glu Tyr Thr Ala
    435                 440                 445

Asp Leu Glu Asp Gly Gly Asn Thr Ile Asn Ile Lys Phe Ala Gly Lys
    450                 455                 460

Glu Thr Pro Glu Thr Pro Glu Glu Pro Lys Glu Glu Val Thr Ile Lys
465                 470                 475                 480

Val Asn Leu Ile Phe Ala Asp Gly Lys Thr Gln Thr Ala Glu Phe Lys
                485                 490                 495

Gly Thr Phe Glu Glu Ala Thr Ala Glu Ala Tyr Arg Tyr Ala Asp Leu
            500                 505                 510

Leu Ala Lys Val Asn Gly Glu Tyr Thr Ala Asp Leu Glu Asp Gly Gly
            515                 520                 525

Tyr Thr Ile Asn Ile Lys Phe Ala Gly Lys Glu Gln Pro Gly Glu Asn
    530                 535                 540

Pro Gly Ile Thr Ile Asp Glu Trp Leu Leu Lys Asn Ala Lys Glu Glu
```

```
                545                 550                 555                 560
Ala Ile Lys Glu Leu Lys Glu Ala Gly Ile Thr Ser Asp Leu Tyr Phe
                565                 570                 575

Ser Leu Ile Asn Lys Ala Lys Thr Val Glu Gly Val Glu Ala Leu Lys
                580                 585                 590

Asn Glu Ile Leu Lys Ala His Ala Gly Glu Glu Thr Pro Glu Leu Lys
                595                 600                 605

Asp Gly Tyr Ala Thr Tyr Glu Glu Ala Glu Ala Ala Lys Glu Ala
    610                 615                 620

Leu Lys Asn Asp Asp Val Asn Asn Ala Tyr Glu Ile Val Gln Gly Ala
625                 630                 635                 640

Asp Gly Arg Tyr Tyr Tyr Val Leu Lys Ile Glu Val Ala Asp Glu Glu
                645                 650                 655

Glu Pro Gly Glu Asp Thr Pro Glu Val Gln Glu Gly Tyr Ala Thr Tyr
                660                 665                 670

Glu Glu Ala Glu Ala Ala Lys Glu Ala Leu Lys Glu Asp Lys Val
            675                 680                 685

Asn Asn Ala Tyr Glu Val Val Gln Gly Ala Asp Gly Arg Tyr Tyr Tyr
    690                 695                 700

Val Leu Lys Ile Glu Asp Lys Glu Asp Glu Gln Pro Gly Glu Glu Pro
705                 710                 715                 720

Gly Glu Asn Pro Gly Ile Thr Ile Asp Glu Trp Leu Leu Lys Asn Ala
                725                 730                 735

Lys Glu Asp Ala Ile Lys Glu Leu Lys Glu Ala Gly Ile Ser Ser Asp
                740                 745                 750

Ile Tyr Phe Asp Ala Ile Asn Lys Ala Lys Thr Val Glu Gly Val Glu
                755                 760                 765

Ala Leu Lys Asn Glu Ile Leu Lys Ala His Ala Glu Lys Pro Gly Glu
                770                 775                 780

Asn Pro Gly Ile Thr Ile Asp Glu Trp Leu Leu Lys Asn Ala Lys Glu
785                 790                 795                 800

Ala Ala Ile Lys Glu Leu Lys Glu Ala Gly Ile Thr Ala Glu Tyr Leu
                805                 810                 815

Phe Asn Leu Ile Asn Lys Ala Lys Thr Val Glu Gly Val Glu Ser Leu
                820                 825                 830

Lys Asn Glu Ile Leu Lys Ala His Ala Glu Lys Pro Gly Glu Asn Pro
                835                 840                 845

Gly Ile Thr Ile Asp Glu Trp Leu Leu Lys Asn Ala Lys Glu Asp Ala
    850                 855                 860

Ile Lys Glu Leu Lys Glu Ala Gly Ile Thr Ser Asp Ile Tyr Phe Asp
865                 870                 875                 880

Ala Ile Asn Lys Ala Lys Thr Ile Glu Gly Val Glu Ala Leu Lys Asn
                885                 890                 895

Glu Ile Leu Lys Ala His Lys Lys Asp Glu Pro Gly Lys Lys Pro
            900                 905                 910

Gly Glu Asp Lys Lys Pro Glu Asp Lys Lys Pro Gly Glu Asp Lys Lys
                915                 920                 925

Pro Glu Asp Lys Lys Pro Gly Glu Asp Lys Lys Pro Glu Asp Lys Lys
                930                 935                 940

Pro Gly Lys Thr Asp Lys Asp Ser Pro Asn Lys Lys Lys Ala Lys
945                 950                 955                 960

Leu Pro Lys Ala Gly Ser Glu Ala Glu Ile Leu Thr Leu Ala Ala Ala
                965                 970                 975
```

```
Ala Leu Ser Thr Ala Ala Gly Ala Tyr Val Ser Leu Lys Lys Arg Lys
            980                 985                 990

<210> SEQ ID NO 10
<211> LENGTH: 299
<212> TYPE: PRT
<213> ORGANISM: Unknown
<220> FEATURE:
<223> OTHER INFORMATION: Description of Unknown: Mammalian
      polypeptide

<400> SEQUENCE: 10

Thr Pro Ala Gly Cys Gly Glu Gln His Met Ile Gly Met Thr Pro Thr
  1               5                  10                  15

Val Ile Ala Val His Tyr Leu Asp Gln Thr Glu Gln Trp Gly Lys Phe
             20                  25                  30

Gly Ile Glu Lys Arg Gln Glu Ala Leu Glu Leu Ile Lys Lys Gly Tyr
         35                  40                  45

Thr Gln Gln Leu Ala Phe Lys Gln Pro Ser Ser Ala Tyr Ala Ala Phe
     50                  55                  60

Asn Asn Arg Pro Pro Ser Thr Trp Leu Thr Ala Tyr Val Val Lys Val
 65                  70                  75                  80

Phe Ser Leu Ala Ala Asn Leu Ile Ala Ile Asp Ser His Val Leu Cys
                 85                  90                  95

Gly Ala Val Lys Trp Leu Ile Leu Glu Lys Gln Lys Pro Asp Gly Val
            100                 105                 110

Phe Gln Glu Asp Gly Pro Val Ile His Gln Glu Met Ile Gly Gly Phe
        115                 120                 125

Arg Asn Ala Lys Glu Ala Asp Val Ser Leu Thr Ala Phe Val Leu Ile
130                 135                 140

Ala Leu Gln Glu Ala Arg Asp Ile Cys Glu Gly Gln Val Asn Ser Leu
145                 150                 155                 160

Pro Gly Ser Ile Asn Lys Ala Gly Glu Tyr Ile Glu Ala Ser Tyr Met
                165                 170                 175

Asn Leu Gln Arg Pro Tyr Thr Val Ala Ile Ala Gly Tyr Ala Leu Ala
            180                 185                 190

Leu Met Asn Lys Leu Glu Glu Pro Tyr Leu Gly Lys Phe Leu Asn Thr
        195                 200                 205

Ala Lys Asp Arg Asn Arg Trp Glu Glu Pro Asp Gln Gln Leu Tyr Asn
    210                 215                 220

Val Glu Ala Thr Ser Tyr Ala Leu Leu Ala Leu Leu Leu Leu Lys Asp
225                 230                 235                 240

Phe Asp Ser Val Pro Pro Val Val Arg Trp Leu Asn Glu Gln Arg Tyr
                245                 250                 255

Tyr Gly Gly Gly Tyr Gly Ser Thr Gln Ala Thr Phe Met Val Phe Gln
            260                 265                 270

Ala Leu Ala Gln Tyr Gln Thr Asp Val Pro Asp His Lys Asp Leu Asn
        275                 280                 285

Met Asp Val Ser Phe His Leu Pro Ser Arg Ser
    290                 295

<210> SEQ ID NO 11
<211> LENGTH: 193
<212> TYPE: PRT
<213> ORGANISM: Yersinia pseudotuberculosis

<400> SEQUENCE: 11

Pro Val Pro Thr Leu Thr Gly Ile Leu Val Asn Gly Gln Asn Phe Ala
```

```
1               5                   10                  15
Thr Asp Lys Gly Phe Pro Lys Thr Ile Phe Lys Asn Ala Thr Phe Gln
                20                  25                  30

Leu Gln Met Asp Asn Asp Val Ala Asn Asn Thr Gln Tyr Glu Trp Ser
            35                  40                  45

Ser Ser Phe Thr Pro Asn Val Ser Val Asn Asp Gln Gly Gln Val Thr
        50                  55                  60

Ile Thr Tyr Gln Thr Tyr Ser Glu Val Ala Val Thr Ala Lys Ser Lys
65                  70                  75                  80

Lys Phe Pro Ser Tyr Ser Val Ser Tyr Arg Phe Tyr Pro Asn Arg Trp
                85                  90                  95

Ile Tyr Asp Gly Gly Arg Ser Leu Val Ser Ser Leu Glu Ala Ser Arg
                100                 105                 110

Gln Cys Gln Gly Ser Asp Met Ser Ala Val Leu Glu Ser Ser Arg Ala
                115                 120                 125

Thr Asn Gly Thr Arg Ala Pro Asp Gly Thr Leu Trp Gly Glu Trp Gly
            130                 135                 140

Ser Leu Thr Ala Tyr Ser Ser Asp Trp Gln Ser Gly Glu Tyr Trp Val
145                 150                 155                 160

Lys Lys Thr Ser Thr Asp Phe Glu Thr Met Asn Met Asp Thr Gly Ala
                165                 170                 175

Leu Gln Pro Gly Pro Ala Tyr Leu Ala Phe Pro Leu Cys Ala Leu Ser
            180                 185                 190

Ile

<210> SEQ ID NO 12
<211> LENGTH: 126
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 12
ggggtcgacg gcggtggcgg tagcggcggt ggcggtagcg gcggtggcgg tagcggcggt      60
gatctggcgc cgcagatgct gcgcgaactg caggaaacca acgcggccct gcaagatgtg     120
cgtgaa                                                                126

<210> SEQ ID NO 13
<211> LENGTH: 126
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 13
ggctcgaggc ccggggtacg ggccggctgc atgccacacg catcgcattc cataacggta      60
tttttcagaa aggtaatttc tttcacttgc tggcgcagca gttcacgcac atcttgcagg     120
gccgcg                                                                126

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer
```

-continued

```
<400> SEQUENCE: 14
gcgccatggg cggtggcggt agcggcggt                                    29

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 15
ggctcgaggc ccggggtacg ggccggctgc                                   30

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 16
gcgccatggg tgatctggcg ccgcagatg                                    29

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 17
ggctcgaggc cacacgcatc gcattccata ac                                32

<210> SEQ ID NO 18
<211> LENGTH: 24
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 18

Gly Pro Gly Pro Gly Gly Gly Gly Ser His His His His His His Gly
1               5                   10                  15

Gly Gly Gly Ser Gly Pro Gly Pro
            20

<210> SEQ ID NO 19
<211> LENGTH: 78
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 19
tcgacggccc gggcccgggc ggtggcggta gccatcatca ccatcatcac ggcggtggcg    60
gtagcggccc gggcccgc                                                  78

<210> SEQ ID NO 20
<211> LENGTH: 78
<212> TYPE: DNA
<213> ORGANISM: Artificial Sequence
```

```
<220> FEATURE:
<223> OTHER INFORMATION: Description of Artificial Sequence: Synthetic
      antisense primer

<400> SEQUENCE: 20
tcgagcgggc cgggccgct accgccaccg ccgtgatgat ggtgatgatg gctaccgcca      60
ccgcccgggc ccgggccg                                                  78

<210> SEQ ID NO 21
<211> LENGTH: 107
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 21
gtcgacgtgg ataacaaatt taataaagaa cagcagaacg ccttctatga aattctgcat     60
ctgccgaacc tgaacgaaga acagcgtaac gcctttattc agagcct                  107

<210> SEQ ID NO 22
<211> LENGTH: 107
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 22
ctcgagttat ttcggggcct gtgcatcgtt cagttttttg gcttctgcca gcagattggc     60
gctctggctc ggatcatctt tcaggctctg aataaaggcg ttacgct                  107

<210> SEQ ID NO 23
<211> LENGTH: 132
<212> TYPE: PRT
<213> ORGANISM: Artificial Sequence
<220> FEATURE:
<223> OTHER INFORMATION: Description of Artificial Sequence: Synthetic
      COMP Z polypeptide

<400> SEQUENCE: 23

Gly Asp Leu Ala Pro Gln Met Leu Arg Glu Leu Gln Glu Thr Asn Ala
1               5                   10                  15

Ala Leu Gln Asp Val Arg Glu Leu Leu Arg Gln Gln Val Lys Glu Ile
            20                  25                  30

Thr Phe Leu Lys Asn Thr Val Met Glu Cys Asp Ala Cys Gly Leu Asp
        35                  40                  45

Gly Pro Gly Pro Gly Gly Gly Ser His His His His His His Gly
    50                  55                  60

Gly Gly Ser Gly Pro Gly Pro Leu Asp Val Asp Asn Lys Phe Asn
65                  70                  75                  80

Lys Glu Gln Gln Asn Ala Phe Tyr Glu Ile Leu His Leu Pro Asn Leu
                85                  90                  95

Asn Glu Glu Gln Arg Asn Ala Phe Ile Gln Ser Leu Lys Asp Asp Pro
            100                 105                 110

Ser Gln Ser Ala Asn Leu Leu Ala Glu Ala Lys Lys Leu Asn Asp Ala
        115                 120                 125

Gln Ala Pro Lys
    130

<210> SEQ ID NO 24
```

<211> LENGTH: 79
<212> TYPE: PRT
<213> ORGANISM: Artificial Sequence
<220> FEATURE:
<223> OTHER INFORMATION: Description of Artificial Sequence: Synthetic
      TBCC (wt) flexible linker

<400> SEQUENCE: 24

Met Gly Ser Ile Ile Asn Glu Thr Ala Asp Asp Ile Val Tyr Arg Leu
1               5                   10                  15

Thr Val Ile Ile Asp Asp Arg Tyr Glu Ser Leu Lys Asn Leu Ile Thr
            20                  25                  30

Leu Arg Ala Asp Arg Leu Glu Met Ile Ile Asn Asp Asn Val Ser Thr
        35                  40                  45

Ile Leu Ala Ser Ile Gly Pro Gly Pro Gly Gly Gly Ser His His
    50                  55                  60

His His His His Gly Gly Gly Gly Ser Gly Pro Gly Pro Leu Glu
65                  70                  75

<210> SEQ ID NO 25
<211> LENGTH: 132
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 25
ccatgggtag cattatcaac gaaaccgccg atgatattgt gtatcgcttg accgtgatca      60
ttgatgatcg ctatgaaagc ctgaaaaatc tgattacctt acgtgccgac cgcctggaaa    120
tgattattaa tg                                                        132

<210> SEQ ID NO 26
<211> LENGTH: 131
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 26
ctcgagcggg cccgggccgc taccgccacc gccgtgatga tggtgatgat ggctaccgcc      60
accgccgggc ccgggccga tgctcgccaa gatggtcgaa acattgtcat taataatcat    120
tccaggcggt c                                                          131

<210> SEQ ID NO 27
<211> LENGTH: 137
<212> TYPE: PRT
<213> ORGANISM: Artificial Sequence
<220> FEATURE:
<223> OTHER INFORMATION: Description of Artificial Sequence: Synthetic
      TBCC iwt j-Z polypeptide

<400> SEQUENCE: 27

Met Gly Ser Ile Ile Asn Glu Thr Ala Asp Asp Ile Val Tyr Arg Leu
1               5                   10                  15

Thr Val Ile Ile Asp Asp Arg Tyr Glu Ser Leu Lys Asn Leu Ile Thr
            20                  25                  30

Leu Arg Ala Asp Arg Leu Glu Met Ile Ile Asn Asp Asn Val Ser Thr
        35                  40                  45

Ile Leu Ala Ser Ile Gly Pro Gly Pro Gly Gly Gly Ser His His
    50                  55                  60

```
His His His His Gly Gly Gly Ser Gly Pro Gly Pro Leu Asp Val
65                  70                  75                  80

Asp Asn Lys Phe Asn Lys Glu Gln Gln Asn Ala Phe Tyr Glu Ile Leu
                85                  90                  95

His Leu Pro Asn Leu Asn Glu Glu Gln Arg Asn Ala Phe Ile Gln Ser
                100                 105                 110

Leu Lys Asp Asp Pro Ser Gln Ser Ala Asn Leu Leu Ala Glu Ala Lys
            115                 120                 125

Lys Leu Asn Asp Ala Gln Ala Pro Lys
    130                 135

<210> SEQ ID NO 28
<211> LENGTH: 137
<212> TYPE: PRT
<213> ORGANISM: Artificial Sequence
<220> FEATURE:
<223> OTHER INFORMATION: Description of Artificial Sequence: Synthetic
      TBCC iS52C j-Z polypeptide

<400> SEQUENCE: 28

Met Gly Ser Ile Ile Asn Glu Thr Ala Asp Asp Ile Val Tyr Arg Leu
1               5                   10                  15

Thr Val Ile Ile Asp Asp Arg Tyr Glu Ser Leu Lys Asn Leu Ile Thr
                20                  25                  30

Leu Arg Ala Asp Arg Leu Glu Met Ile Ile Asn Asp Asn Val Ser Thr
            35                  40                  45

Ile Leu Ala Cys Ile Gly Pro Gly Pro Gly Gly Gly Ser His His
50                  55                  60

His His His His Gly Gly Gly Gly Ser Gly Pro Gly Pro Leu Asp Val
65                  70                  75                  80

Asp Asn Lys Phe Asn Lys Glu Gln Gln Asn Ala Phe Tyr Glu Ile Leu
                85                  90                  95

His Leu Pro Asn Leu Asn Glu Glu Gln Arg Asn Ala Phe Ile Gln Ser
                100                 105                 110

Leu Lys Asp Asp Pro Ser Gln Ser Ala Asn Leu Leu Ala Glu Ala Lys
            115                 120                 125

Lys Leu Asn Asp Ala Gln Ala Pro Lys
    130                 135

<210> SEQ ID NO 29
<211> LENGTH: 138
<212> TYPE: PRT
<213> ORGANISM: Artificial Sequence
<220> FEATURE:
<223> OTHER INFORMATION: Description of Artificial Sequence: Synthetic
      TBCC iC60 j-Z polypeptide

<400> SEQUENCE: 29

Met Gly Ser Ile Ile Asn Glu Thr Ala Asp Asp Ile Val Tyr Arg Leu
1               5                   10                  15

Thr Val Ile Ile Asp Asp Arg Tyr Glu Ser Leu Lys Asn Leu Ile Thr
                20                  25                  30

Leu Arg Ala Asp Arg Leu Glu Met Ile Ile Asn Asp Asn Val Ser Thr
            35                  40                  45

Ile Leu Ala Ser Ile Gly Pro Gly Pro Gly Gly Cys Gly Gly Ser His
50                  55                  60

His His His His Gly Gly Gly Gly Ser Gly Pro Gly Pro Leu Asp
65                  70                  75                  80
```

-continued

```
Val Asp Asn Lys Phe Asn Lys Glu Gln Gln Asn Ala Phe Tyr Glu Ile
                 85                  90                  95

Leu His Leu Pro Asn Leu Asn Glu Glu Gln Arg Asn Ala Phe Ile Gln
            100                 105                 110

Ser Leu Lys Asp Asp Pro Ser Gln Ser Ala Asn Leu Leu Ala Glu Ala
        115                 120                 125

Lys Lys Leu Asn Asp Ala Gln Ala Pro Lys
    130                 135
```

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 30
tcgaccatct tggcgtgcat cggcccgggc ccg                            33

<210> SEQ ID NO 31
<211> LENGTH: 32
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 31
cgggcccggg ccgatgcacg ccaagatggt cg                             32

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: Synthetic
      sense primer

<400> SEQUENCE: 32
ccgggcccgg gcggttgcgg cggtagccat catcac                         36

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Synthetic
      antisense primer

<400> SEQUENCE: 33
atgatggcta ccgccgcaac cgcccgggcc cgg                            33

<210> SEQ ID NO 34
<211> LENGTH: 53
<212> TYPE: PRT
<213> ORGANISM: Staphylothermus marinus

<400> SEQUENCE: 34

```
Met Gly Ser Ile Ile Asn Glu Thr Ala Asp Asp Ile Val Tyr Arg Leu
1               5                  10                  15

Thr Val Ile Ile Asp Asp Arg Tyr Glu Ser Leu Lys Asn Leu Ile Thr
            20                  25                  30

Leu Arg Ala Asp Arg Leu Glu Met Ile Ile Asn Asp Asn Val Ser Thr
        35                  40                  45
```

```
Ile Leu Ala Ser Ile
    50

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 35

Gly Pro Gly Pro
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 36

Gly Gly Gly Gly Ser
1               5

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      linker
<220> FEATURE:
<221> NAME/KEY: misc_feature
<222> LOCATION: (1)..(20)
<223> OTHER INFORMATION: This sequence may encompass 1-4
      "Gly Gly Gly Gly Ser" repeating units

<400> SEQUENCE: 37

Gly Gly Gly Gly Ser Gly Gly Gly Gly Ser Gly Gly Gly Gly Ser Gly
1               5                   10                  15

Gly Gly Gly Ser
            20

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 38

Gly Gly Gly Gly Ser Gly Gly Gly Gly Ser Gly Gly Gly Gly Ser
1               5                   10                  15

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 39

His His His His His His
```

-continued

```
<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 40

Gly Pro Gly Pro His His His His His His Gly Pro Gly Pro
1               5                   10

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 41

Gly Gly Gly Gly Ser His His His His His His Gly Gly Gly Gly Ser
1               5                   10                  15
```

DRUG TRANSPORTER, AND ADJUVANT AND VACCINE EACH UTILIZING SAME

CROSS-REFERENCE TO RELATED APPLICATIONS

The present application is a 35 U.S.C. §371 National Stage patent application of International patent application PCT/JP2010/051915, filed on Feb. 10, 2010, which claims priority to Japanese patent application JP 2009-028134, filed on Feb. 10, 2009.

TECHNICAL FIELD

The present invention relates to a novel drug delivery vehicle, and more specifically, to a drug delivery vehicle which is highly versatile and safe, which is capable of allowing the drug to reach a target cell or tissue effectively, and which is capable of improving the immunostimulating effect of an adjuvant and the immunogenicity of a vaccine by allowing the adjuvant and the vaccine to be carried thereon as well as an adjuvant and a vaccine utilizing the same.

BACKGROUND ART

A drug delivery system which is specific to a cell and a tissue has been developed for preventing infectious diseases and establishing new therapeutic methods against cancers. Various vaccines and adjuvants (immunopotentiator) for protection against infectious diseases have so far been developed. While a conventional vaccine has mostly been obtained by attenuating or inactivating a virus or a bacteria, a recent advancement in gene engineering technologies enabled a large scale production of an antigen derived from a specific pathogen, whereby enabling development of a further safer component vaccine. However, there occurred a problem, on the other hand, that the immunogenicity of a highly purified recombinant protein was reduced.

In order to improve the immunogenicity of a component vaccine, a technology which utilizes a fusion protein of an antigen and a complement 4 binding protein (C4bp) as a vaccine was proposed (Patent document 1). Nevertheless, this technology had a problem that it had no ability of transporting an antigen site-specifically, although it allowed for association of the antigen.

In addition, since a low immune response is elicited on the mucosal surface especially when using a mucosal, e.g., oral or nasal vaccine among vaccines, no sufficient effect can be obtained actually without an effective mucosal adjuvant (immunopotentiator) even if an antigen having a high protective effect was found. There are known clinically applicable adjuvants such as an aluminum salt, which however can not exhibit an effectiveness on a mucosa, and may induce a problematic side reaction. There are known mucosal adjuvants such as cholera toxin (CT), which is however limited to be used only on an experimental level from a viewpoint of safety since it is a toxin-related molecule. Moreover, although these adjuvants are administered in mixtures with vaccines, such a method of use does not allow the adjuvant to penetrate the mucosal barrier, resulting in a difficulty in exerting a sufficient effect.

On the other hand, a technology for improving the solubility or the stability of a protein fused with a coiled coil structure-forming protein is proposed (Patent document 2), and the creation of a novel functional substance utilizing a coiled coil structured protein is expected. In addition, a technology of drug targeting and delivery system by means of a peptide fused with a coiled coil protein employing the coiled coil structure-forming protein is also proposed (Patent document 3). This is a method for producing a nano particle utilizing a coiled coil protein, and is a technology for utilizing the latter as a scaffold for delivering the fused peptide. Nevertheless, since this is a technology for delivering the fused peptide passively rather than actively, it results in poor efficiency. While a peptide should be used as a targeted functional substance for the purpose of an active delivery, the nano particle involves a problem that the fused peptide fails to exhibit the target receptor binding function sufficiently due to a steric hindrance.

RELATED ART DOCUMENTS

Patent Documents

Patent document 1: Japanese Translation of PCT International Application Publication No. JP-T-2007-528210
Patent document 2: Japanese Translation of PCT International Application Publication No. JP-T-2008-514585
Patent document 3: Japanese Translation of PCT International Application Publication No. JP-T-2006-519781

SUMMARY OF THE INVENTION

Problems to be Solved by the Invention

Thus, a transportation system capable of allowing a vaccine or adjuvant to reach the target cell or tissue efficiently and improving the vaccine's immunogenicity, or capable of enhancing the adjuvant's immunopotentiating effect is desired to be developed, and accordingly an objective of the invention is to provide such a drug delivery vehicle and a vaccine or adjuvant utilizing the same.

Means for Solving the Problems

As a result of extensive studies for solving the above-mentioned problems, the present inventors found that by allowing a vaccine or adjuvant molecule to be carried on a carrier formed by fusing a multimeric protein having a coiled coil structure in a compact state without forming a nano structure with a ligand molecule to an immune response cell receptor in a design reducing steric hindrance an efficient transportation to a target tissue or cell becomes possible while exhibiting an excellent immunopotentiating effect, and the present invention has been completed.

Thus, the present invention is a drug delivery vehicle containing a multimeric protein having a coiled coil structure and a ligand molecule to an immunocompetent cell receptor.

Also, the present invention is an adjuvant formed by binding an adjuvant molecule with the above-mentioned drug delivery vehicle.

Furthermore, the present invention is a vaccine formed by binding a vaccine molecule with the above-mentioned drug delivery vehicle.

Effects of the Invention

According to the present invention, it is possible to allow an adjuvant or vaccine to reach a target tissue or cell efficiently and to enhance the vaccine's immunogenicity or the adjuvant's immunopotentiating effect. Furthermore, a high flexibility in designing its constituent molecule members allows for a high versatility in addition to an excellent safeness.

MODE FOR CARRYING OUT THE INVENTION

Figure 1:
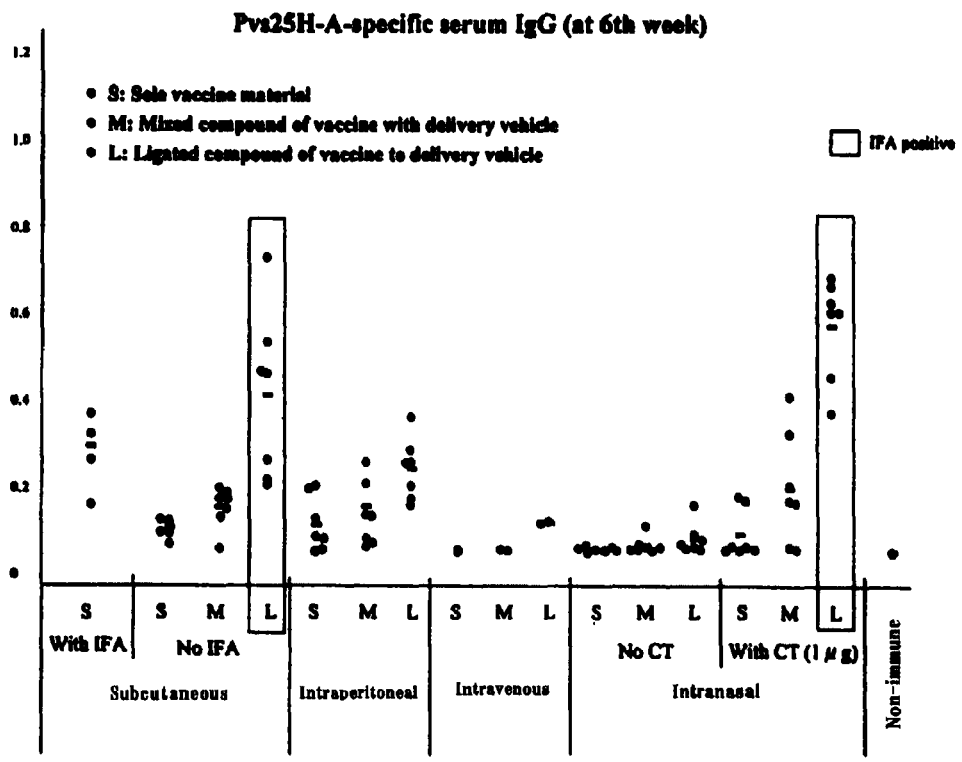
FIG. 1 shows the ELISA data in Example 3.

A drug delivery vehicle of the present invention contains a multimeric protein having a coiled coil structure and a ligand molecule to a receptor of an immunocompetent cell.

Various multimeric proteins having coiled coil structures can be employed including proteins described for example in "The structure of alpha-helical coiled coils" (Adv Protein Chem. 2005; 70: 37-78 Andrei N. Lupas, Markus Gruber et al.). While the number of the monomers constituting a multimeric protein is not particularly limited, dimer to heptamer are preferred and dimer to pentamer are especially preferred. Within this range, the thermostability is excellent and the affinity for the receptor of an immunocompetent cell is improved, resulting in an enhanced immunogenicity. While the number of the amino acid residues is not particularly limited, it is usually 20 to about 80, and preferably 50 to 60. Within this range, stability and compactness are obtained together with an advantage of serving as a scaffold for chemical binding of antigens and the like.

Preferred multimeric proteins having coiled coil structures may typically be parallel-type coiled coil structured multimeric protein including COMP (cartilage oligomeric matrix protein, pentamer), tetrabrachion coiled core (TBCC, tetramer) derived from a thermophilic microorganism *Staphylothermus marinus* and having a heat resistance at 130° C. or below, and a σ1 protein derived from Reovirus and exhibiting adhesiveness to an M cell present on a mucosal epithelium. Among these, COMP and TBCC are employed preferably. COMP is preferred since it has an extremely stable coiled coil structure and a high heat resistance. TBCC is further preferred when combining with unstable molecules since its thermostability is as extremely high as 130° C. (J. Mol. Biol. 1995; 245, 385-401 Peter J, Nitsch M et al.). On the other hand, a hepatitis delta antigen (HDAg, dimer) derived from Hepatitis delta virus having an antiparallel-type coiled coil structure can also be employed. Such an antiparallel-type coiled coil structure is advantageous since it has a spacer-like function by itself and can bind with a receptor of an immunocompetent cell in a further compact manner.

Amino acid sequences are shown in SEQ ID NO:1 for COMP, SEQ ID NO:2 for a tetrabrachion, SEQ ID NO:3 for a σ 1 protein, SEQ ID NO:4 for a hepatitis delta antigen and SEQ ID NO:34 for a TBCC. A coiled coil structured multimeric protein of the present invention may be a polypeptide consisting of an amino acid sequence of an oligomerization domain (OD) among the amino acid sequences listed above. SEQ ID NO:5 is an OD of COMP, a conserved region of which is shown in SEQ ID NO:6. Also included are a polypeptide consisting of an amino acid sequence resulting from deletion, substitution or addition of one or several amino acids in the amino acid sequences listed above. Further included are a polypeptide consisting of an amino acid sequence whose homology with an amino acid sequence described above is 80% or more, preferably 90% or more, more preferably 95% or more.

On the other hand, a ligand molecule to a receptor of an immunocompetent cell may be selected from various polypeptides, oligosaccharides, nucleic acids and lipids, and those which may typically be exemplified are a *Staphylococcus* Protein A-derived antibody binding domain, a B1 domain (SpG-B) of a Group G *Streptococcus* G148-derived G protein (SpG), a *Finegoldia magna* (*Peptostreptococcus mugnus*)-derived L protein, a complement system molecule C3d, and *Yersinia pseudotuberculosis* invasin and the like. Amino acid sequences are shown in SEQ ID NO:7 for a Protein A-derived antibody binding domain (Z domain), SEQ ID NO:8 for a *Streptococcus* G148-drived G protein B1 domain, SEQ ID NO:9 for a *Finegoldia magna* (*Peptostreptococcus mugnus*)-derived L protein, SEQ ID NO:10 for a complement system molecule C3d, and SEQ ID NO:11 for *Yersinia pseudotuberculosis* invasin, and the ligand molecule to the immunocompetent cell receptor according to the present invention includes not only the proteins shown by the particular amino acid sequences described above but also a polypeptide consisting of an amino acid sequence resulting from deletion, substitution or addition of one or several amino acids in the amino acid sequences listed above. Further included are a polypeptide consisting of an amino acid sequence whose homology with an amino acid sequence described above is 80% or more, preferably 90% or more, more preferably 95% or more.

Among these, the *Staphylococcus* protein A-derived antibody binding domain is constituted from 58 amino acid residues and is a protein having a molecular weight of about 6 kDa, whose structure is in a compact shape consisting of three α-helixes, a single α-helix of which interacts with the Fc or the Fab region of an immunoglobulin. An SpG constituent domain B1 domain (SpG-B) has a high avidity with a B cell receptor (BCR). On the other hand, a complement system molecule C3d which is one of the effector factors of an innate immunity is preferable since it binds to CR2(CD21) which is one of the complement receptors present in B cells and follicular dendritic cells while CR2 is an important component of a B cell coreceptor complex and enhances the sensitivity of B cells to an antigen whereby functioning not only as a ligand molecule but also as an adjuvant. Furthermore, when a *Yersinia pseudotuberculosis* invasin is used, a β 1 integrin expressed on an M cell can be targeted.

While a drug delivery vehicle of the present invention is formed by binding a multimeric protein having a coiled coil structure chemically or in a gene engineering manner with a ligand molecule to the receptor of a immunocompetent cell, it is preferably one obtained by expressing a fusion protein of a monomeric protein constituting a multimeric protein having a coiled coil structure and a high molecular stability with a ligand protein to a receptor of an immunocompetent cell which is then subjected to an in vivo or in vitro association whereby forming a multimer. The fusion between the two domains in the fusion protein may be accomplished in either positions of N and C terminals, and the ligand protein to the receptor of the immunocompetent cell may be fused with the N or C terminal of the monomeric protein constituting the multimeric protein having the coiled coil structure. Alternatively, a chemical binding with a reactive substitute in the monomeric protein is acceptable, although a binding to the terminal in a gene engineering manner is preferable. While the ligand protein can be fused with the monomeric protein constituting the multimeric protein having the coiled coil structure directly or via a linker sequence, the fusion via a linker sequence which is a 4 to 30 amino acid residue-carrying, preferably a 10 to 25 amino acid residue-carrying peptide is preferable because of its ability of reducing the intermolecular interference upon forming a conformation as well as its flexibility serving advantageously upon binding with the receptor.

While such a linker sequence is not particularly limited, it may for example be a sequence formed by combining GPGP (SEQ ID NO: 35) or GGGGS ($G_4S$) (SEQ ID NO: It is also possible to use as a linker a sequence formed by repeating ($G_4S$) 1 to 4 times (SEQ ID NO: 37) $4G_4S)_1$ (SEQ ID NO: 36) to $(G_4S)_3$ (SEQ ID NO: 38)), which may further be combined with GPGP (SEQ ID NO: 35). The linker sequence may have a purification tag inserted therein, which may for example be Hisx6 ($H_6$) (SEQ ID NO: 39). A preferred example is GPGP ($G_4S)H_6(G_4S)$GPGP (SEQ ID NO: 18). In this sequence, the moiety ($G_4S$) (SEQ ID NO: 36) may be replaced with a repeating sequence (($G_4S$), (SEQ ID NO: 36) to $(G_4S)_3$ (SEQ ID NO: 38)). Furthermore, sequences $GPGPH_6GPGP$ (SEQ ID NO: 40) and $G_4SH_6G_4S$ (SEQ ID NO: 41) may also be employed as linker sequences.

A fusion protein containing a monomeric protein constituting a multimeric protein having a coiled coil structure and a ligand protein to a receptor of an immunocompetent cell mentioned above can be produced by an ordinary gene engineering technique. Thus, the base sequence of a DNA encoding the amino acid sequence of the above-mentioned monomeric protein constituting a multimeric protein having a coiled coil structure and the base sequence of a DNA encoding the amino acid sequence of the ligand protein to a receptor of an immunocompetent cell are ligated on an expression vector, which is then employed to transform an appropriate host whereby obtaining an expression product (intended fusion protein) of a fused gene.

While the expression vector may for example be a plasmid vector, a phage vector, a viral vector, an artificial chromosome vector and the like, a plasmid vector is preferable from the viewpoint of simple handling and cost. Typically, pET-22b and pET-21d may be exemplified when the host is an *E. coli*. The expression vector may contain a regulatory sequence having a regulatory function for gene expression such as a promoter or an enhancer. The ligation of the base sequence of the DNA encoding a fusion protein to the expression vector can be accomplished by known methods such as a restriction enzyme terminal ligation.

By using the expression vector thus produced to transform a host, a transformant containing the expression vector can be obtained. The host may for example be those known per se such as *E. coli*, yeast, mammalian cell lines and the like. The *E. coli* may for example be BL21 strain, DH5 alpha strain and the like. The yeast may for example be *Pichia pastoris, Saccharomyces cerevisiae* and the like.

Introduction of the expression vector to a host cell can be performed by any known method depending on the host cell such as a calcium phosphate method, an electroporation method, a lipofection method and the like. After introduction, cultivation in a medium containing a selection marker allows for selection of a transformant which is a host cell now having the above-mentioned expression vector introduced therein.

The transformant thus obtained is cultured under a preferable condition, whereby producing a fusion protein. The fusion protein thus expressed undergoes oligomerization spontaneously to form a multimer, which is then accumulated in the cell or secreted out of the cell. The protein thus obtained is further isolated or purified by an ordinary purification method. The purification method here may for example be any of various methods such as an affinity chromatography, an ion exchange chromatography, a hydrophobic interaction chromatography, a gel filtration chromatography and the like.

A drug delivery vehicle consisting of the fusion protein thus obtained may for example be one containing a polypeptide consisting of the amino acids shown in Sequence Listing 23. This is formed as a result of binding of a conserved region of the oligomerization domain of COMP (SEQ ID NO:6) and an antibody binding domain derived from *Staphylococcus* Protein A (SEQ ID NO:7) via a flexible linker [GPGP($G_4S$) $H_6(G_4S)$GPGP] (SEQ ID NO: 18) and forms a pentamer. The drug delivery vehicle of the present invention includes not only the protein shown by this amino acid sequences but also a polypeptide consisting of an amino acid sequence resulting from deletion, substitution or addition of one or several amino acids in the amino acid sequences listed above. Further included are a polypeptide consisting of an amino acid sequence whose homology with an amino acid sequence described above is 80% or more, preferably 90% or more, more preferably 95% or more.

The drug delivery vehicle thus obtained which consists of a fusion protein can carry various drugs such as an adjuvant molecule, a vaccine molecule, a biologically active molecule (drug molecule) and the like, among which an adjuvant molecule or a vaccine molecule is carried on preferably. The adjuvant molecule or vaccine molecule which can be employed is not particularly limited, and may be any of those known per se. Typically, the adjuvant molecule may for example be cholera toxin (CT), cholera toxin B subunit (CTB), cholera toxin A subunit (CTA), *Bordetella-pertussis* toxin (PT), *Bordetella-pertussis* toxin S1 subunit (PTS1), Toll-like receptor 9 (TLR9) ligand, Toll-like receptor 4 (TLR4) ligand and the like. Among these, CTA and PTS1 are preferable since activation of a NF-κ B pathway can be induced. On the other hand, the TLR9 ligand may for example be an oligodeoxynucleotides having a non-methylated CpG motif (CpG ODN), while the TLR4 ligand may for example be a monophosphoryl lipid A (MPLA) resulting from detoxifying a lipid A which is a part of endotoxin.

An action mechanism when utilizing these adjuvants involves as a main uptake route a foreign antigen presenting route by MHC class II via an endosome, and is considered mainly to be an immunostimulating effect attributable to an antibody response enhancement.

On the other hand, a cationic peptide having a membrane permeating function can also be used as an adjuvant molecule, and those exemplified typically are membrane dislocation sequences such as polyarginine, polylysine, $Tat_{49-57}$ peptide and penetratin as well as signal sequence-derived peptides and the like. These are effective also in inducing a cellular immunity, and considered to be effective against intracellular parasitizing bacteria, cancer, allergy and the like.

As a vaccine molecule, a vaccine candidate antigen originated in various arthropod-mediated diseases and parasitic, bacterial or viral infections can be utilized and those exemplified typically are antigens derived from pathogens such as Japanese encephalitis virus coat protein, *Plasmodium* surface protein and *Schistosoma japonicum*, including polypeptides containing epitopes thereof. These are considered to be effective in antibody production and cellular immunity induction.

Such an adjuvant molecule or a vaccine molecule is bound to a drug delivery vehicle as a fusion protein directly or via a linker sequence chemically or in a gene engineering manner. The binding of the adjuvant molecule or the vaccine molecule to the delivery vehicle fusion protein may occur in any possible position, and the binding may be to a monomeric protein constituting a multimeric protein having a coiled coil structure at the N terminal or C terminal position opposite to the ligand protein to an immunocompetent cell receptor, and, alternatively, the binding may be to a reactive substituent in the monomeric protein constituting a multimeric protein, although the fusion to the terminal is preferable.

A technique for a chemical binding uses a crosslinker to effect a binding while utilizing an amino group or a thiol group (SH group) present in the protein or an aldehyde group in a saccharide chain present in the protein, while the functional group employed is not limited. For example, an exemplified method involves a reaction between an SH group in a monomeric protein constituting a multimeric protein having a coiled coil structure and an amino group in an adjuvant or vaccine protein, and more typically the binding can be accomplished by incubating a fusion protein obtained by a reducing treatment using a reducing agent such as dithiothreitol (DTT) and an adjuvant or vaccine protein having a pyridyl disulfide group introduced therein from N-succinyl-3-(2-pyridylthio)propionate (SPDP). One or more adjuvant molecules or vaccine molecules may be bound to the multimeric protein having a coiled coil structure. A crosslinker may be of a chemical substance-derived homofunctional or heterofunctional type, and can be utilized with no limitation. Furthermore, the chemical binding can be accomplished by means of a bond utilizing interaction between biological molecules such as biotin and avidin.

On the other hand, a binding in a gene engineering manner can be accomplished by ligating the base sequence of a DNA encoding the amino acid sequence of a monomeric protein constituting a multimeric protein having a coiled coil structure described above and the base sequence of a DNA encoding the amino acid sequence of the ligand protein to a receptor of an immunocompetent cell which are then subcloned into an expression vector. It is also possible to ligate the base sequence of a DNA encoding the amino acid sequence of an adjuvant protein or vaccine protein successively which is then expressed in a manner similar to that described above whereby obtaining a fusion protein as a gene expression product of an entire fusion gene constituted from three moieties. The adjuvant or vaccine-delivery vehicle-fused protein thus expressed also undergoes a self-assembly whereby forming a multimer.

The fusion adjuvant or vaccine thus obtained can be administered by any suitable route including oral, nasal, subcutaneous, intravenous, intraperitoneal routes and the like. While the dose of the adjuvant or vaccine may appropriately be selected depending on the type of the adjuvant or vaccine, it is usually about 5 to 100 µg as a single dose for an adult when using a vaccine obtained by binding Pvs25 which is a transmission blocking antigen of the *Plasmodium vivax*.

An adjuvant or vaccine of the present invention is capable of reaching a target cell or tissue efficiently and also capable of enhancing an immunostimulating effect or immunogenicity, possibly because of an ability of presenting an antigen directly to an immunocompetent cell, which leads to a promoted efficiency of the antigen uptake and an enhanced antigen producing response and cellular immunity while forming a multimer, which leads to an aggregation or crosslinking of the immunocompetent cell receptor, which allows a cytophysiological stimulation to be given to the immunocompetent cell efficiently, whereby enhancing a subsequent intracellular signaling transmission induction.

EXAMPLE

The present invention is described in further detail in Examples shown below which is not intended to restrict the invention.

Example 1

Production of COMP-Z Delivery Vehicle (Cloning of COMP OD)

The following method was employed to clone the oligomerization domain (oligomerization domain: OD) of COMP. Thus, in order to obtain a product having the amino acid sequence of $(G_4S)_3$ (SEQ ID NO: 38) added as a spacer sequence to 55 amino acid residues of COMP OD (SEQ ID NO:5), a sense primer SEQ ID NO:12 and an antisense primer SEQ ID NO:13 were produced, annealed and then introduced into a pCR2.1 vector, whereby accomplishing a subcloning.

After completion of the subcloning of COMP OD, the base sequence was verified, and a sense primer SEQ ID NO:14 and an antisense primer SEQ ID NO:15 were employed to amplify a COMP OD gene by a PCR, followed by digestion with restriction enzymes NcoI and XhoI, followed by subcloning into an *E. coli* expression vector pET-22b at the NcoI-XhoI site, followed by an ordinary calcium phosphate method to transform into an *E. coli* DH5 alpha. Then a screening on the basis of ampicillin as a drug resistance marker present in the vector was conducted to select an intended gene-transduced clone. This clone was further transformed into a protein-expressing *E. coli* strain BL21 (DE3) by a calcium phosphate method, followed by screening with ampicillin, followed by construction of a COMP OD-expressing construct. This expression strain was pre-cultured one whole day and night at 37° C. in 100 ml of an ordinary LB-ampicillin-containing (LB-Amp) medium, and then inoculated at $OD_{600nm}$=0.1 to four tubes each containing 250 ml of the LB-Amp medium, which were cultured for 1.5 hours at 37° C. At this time point, the turbidity $OD_{600nm}$ was measured to ensure an $OD_{600nm}$ of 0.4 to 0.6, and then isopropyl-β-thiogalactopyranoside (IPTG) was added at a final concentration of 1 mM, and a whole day and night culture at 37° C. was conducted to induce the expression of the protein. After inducing the expression, the culture supernatant was separated by centrifugation (8,000 rpm, 20 min, 4° C., 2 times) followed by filtration through a 0.45 µm filter, followed by purification by an affinity chromatography on a His-tag column, followed by a 15% acrylamide gel SDS-PAGE of an aliquot of the purified protein, whereby verifying the expression of the COMP OD moiety.

Then, the COMP OD conserved region was selected exclusively and a COMP OD employing a compacter 46 amino acid sequence (SEQ ID NO:6) was expressed by the method described below (COMP(Gly27-Gly72)).

For amplifying the COMP(Gly27-Gly72) moiety exclusively, a previously constructed pET-22b-COMP OD was employed as a template together with a sense primer SEQ ID NO:16 and an antisense primer SEQ ID NO:17 to conduct a PCR whereby amplifying the COMP(Gly27-Gly72) moiety, followed by digestion with restriction enzymes NcoI and XhoI, followed by subcloning into an expression vector pET-22b at the NcoI-XhoI site, whereby constructing a COMP (Gly27-Gly72) expression construct (pET-22b-COMP (Gly27-Gly72)). After verifying the base sequence, an expression analysis was conducted whereby discovering that this construct underwent a secretion expression of COMP (Gly27-Gly72) predominantly in the culture supernatant.

(Introduction of Linker Region)

Subsequently, a linker region was introduced into the COMP (Gly27-Gly72) moiety. The linker region was GPGP (SEQ ID NO: 35) combined with $G_4S$ (SEQ ID NO: 36), with which Hisx6 (SEQ ID NO: 39) used as a protein purification tag was further employed in the linker region to form a linker region GPGP$(G_4S)H_6(G_4S)$GPGP (SEQ ID NO:18), which was introduced into the C terminal of the COMP OD. Typically, the linker was introduced by using a 5'-phosphorylated sense primer SEQ ID NO:19 and an antisense primer SEQ ID NO:20 to anneal the linker region, followed by subcloning into the XhoI site of the pET-22b-COMP (Gly27-Gly72), whereby accomplishing construction (pET-22b-COMP (Gly27-Gly72)-flexible linker). After verifying the base sequence, an expression analysis was conducted whereby discovering that this construct underwent a secretion expression of the COMP(Gly27-Gly72)-flexible linker predominantly in the culture supernatant similarly to COMP(Gly27-Gly72).

(Fusion of Ligand Moiety)

The above-mentioned COMP(Gly27-Gly72)-flexible linker was subjected to the following method to construct a ligand moiety. As a ligand, an antibody binding domain (Z domain) which is a B domain homolog derived from a *Staphylococcus aureus*-derived Protein A (SpA) was employed (SEQ ID NO:7). This Z domain was fused to the C terminal of the COMP(Gly27-Gly72)-flexible linker constructed previously in a gene engineering manner. Typically, a synthetic oligo of a sense primer SEQ ID NO:21 and an antisense primer SEQ ID NO:22 was produced, annealed and then introduced into a pCR2.1 vector, whereby completing the cloning of the Z domain. After verifying the base sequence followed by digestion with restriction enzymes SalI and XhoI, followed by subcloning into the XhoI site of the pET-22b-COMP(Gly27-Gly72)-flexible linker, whereby completing the construction (pET-22b-COMP-Z).

(Methods of Culture, Expression Induction and Purification of COMP-Z Protein)

10 µl of a frozen stock of an *E. coli* strain BL21 (DE3) containing pET-22b-COMP-Z was inoculated to 100 ml of an LB-Amp medium, which was pre-cultured a whole day and night at 37° C. Subsequently, inoculation was conducted at $OD_{600\ nm}$=0.1 to four tubes each containing 250 ml of the LB-Amp medium, which were cultured for 1.5 hours at 37° C. At this time point, the turbidity $OD_{600\ nm}$ was measured to ensure an $OD_{600\ nm}$ of 0.4 to 0.6, and then isopropyl-β-thiogalactopyranoside (IPTG) was added at a final concentration of 1 mM, and a whole day and night culture at 37° C. was conducted to induce the expression of the protein. After inducing the expression, all cultures were combined and subjected to a centrifugation (8,000 rpm, 20 min, 4° C., 2 times) to separate into the cells and the culture supernatant. Upon this, an aliquot of the culture supernatant was recovered for an expression analysis. Subsequently, the culture supernatant was filtered through a 0.45 µm filter, and prepared for applying to a chromatography. For the affinity chromatography of COMP-Z, 10 ml of an IgG Sepharose resin (GE healthcare) was filled in an open column, whereby preparing a purification column. A TST buffer solution (pH8.0) was used as a column equilibration solution in a volume 2 to 3 times the column volume until reaching equilibration at pH8.0, then a 0.5M acetic acid solution (pH3.5) was loaded in a volume 2 to 3 times the column volume. Equilibration at pH3.5 was ensured here again and this step was repeated twice and finally the TST buffer solution (pH8.0) was used until reaching equilibration at pH8.0 (TST→acetic acid→TST→acetic acid→TST).

Subsequently, a sample solution prepared was applied to the column by gravity or using a peristaltic pump and the like, whereby conducting an affinity chromatography.

After applying the sample, the column was then washed. Washing was conducted using a 10-volume TST buffer solution (pH8.0) followed by a 2-volume 0.5M ammonium acetate solution (pH5.5). After washing, elution was conducted using 50 ml of an elution buffer (0.5M acetic acid solution (pH3.5)). The culture supernatant, the flow-through fraction, the wash fraction, and the elution fraction were analyzed by a 15% acrylamide gel SDS-PAGE. After running, the expression pattern was examined to ensure the expression in the elution fraction, followed by concentration using an ultrafiltration membrane (Amicon Ultra-4 50K), followed by replacement with PBS. A BCA method employing a BCA Protein Assay Reagent (bicinchoninic acid) manufactured by PIERCE was employed for quantification, which revealed that the concentration of the COMP-Z fusion protein was 6 mg/ml while the total protein was 30 mg.

(Endotoxin Removal Treatment of COMP-Z)

Since an endotoxin was suspected to be contaminating a recombinant protein produced with an *E. coli*, the endotoxin was removed and the endotoxin concentration was assayed prior to conducting an immune experiment.

Since the endotoxin was as small as about 10 kDa while COMP-Z is a high molecular weight protein, a treatment was conducted using a 50 kDa dialysis membrane. The exterior solution employed was a PBS, which was exchanged every several hours at 4° C. over a finally whole day and night dialysis (dialysis of about 4 to 5 cycles each with 1 L of the PBS).

A sample thus dialyzed was applied onto an endotoxin removal column (PIERCE; Detoxi-Gel Endotoxin Removal Gel) where the endotoxin was removed. A sample after passing the endotoxin removal column was subjected to a BCA quantification and a limulus test (LAL) was conducted to assay the endotoxin concentration.

Thus, using a LAL Pyrogen Single Test for 25 cycles, a sample diluted to a final volume of 0.25 ml was assayed. The sample was diluted with an endotoxin-free water. A sample solution adjusted at a required concentration was injected into a vial using a syringe, mixed gently, placed in a box or equivalent for avoiding fall down, where it was allowed to react for 1 hour at 37° C. After the reaction, the vial was taken out gently and inverted, and the judgment was endotoxin positive when the content was solidified while endotoxin negative when the content was not solidified or the solution partly dropped down as being dissolved. Since the endpoint is defined as the level just before the dilution level at which the judgment becomes negative, from which the number of the endotoxin units was calculated, and when a level of 500 pg endotoxin/µg of protein or higher was observed then the sample was applied again to the endotoxin removal column, and the same procedure was repeated until a level of 500 pg endotoxin/µg of protein or lower was observed.

Example 2

Production of Vaccine-Delivery Vehicle Fusion Complex (1)

Pvs25 which is a transmission blocking antigen of the *Plasmodium vivax* was fused with COMP-Z chemically utilizing an SH group present in COMP-Z. The vaccine antigen Pvs25 employed was a Pvs25H A form (Pvs25H-A) having a uniform conformation expressed in a yeast *Pichia pastoris*. As a crosslinker required for the fusion, an SPDP was employed and the following reaction schemes were employed to establish a fusion complex COMP-Z/Pvs25H-A.

The fusion was conducted using a COMP-Z pentamer (1 mg; 373 µl; 13,793 pmol), Pvs25H-A (2.84 mg; 499 µl; 137, 864.08 pmol) (the molecular weight of COMP-Z was 72.5 kDa, the molecular weight of Pvs25H-A was 20.6 kDa, and COMP-Z to Pvs25H-A was 1 mol to 10 mol).

(Reducing Treatment)

First, a reducing treatment was conducted for ensuring an SH group in a reduced form in COMP-Z. While COMP-Z has an SH group in a reduced form even when being expressed in an E. coli, the number of available SH groups was desired to be increased. After adding 1 mg of COMP-Z to 1,379.3 nmol of DTT, reaction was conducted for 30 minutes at 37° C. Thereafter, DTT was removed by an ultrafilter (Amicon Ultra-4 10K; 5,000×g 20 min×4 times with PBS).

(Fusion Treatment)

Immediately before use, 2 mg of an SPDP was dissolved in 320 μl of DMSO to prepare a 20 mM SPDP solution. 45 μl of the 20 mM SPDP solution was combined with 2.84 mg of Pvs25H-A (adjusted to 1.5 ml with a PBS), and incubated at room temperature for 60 minutes (production of pyridyldithiol-activated Pvs25H-A). Purification was conducted using an ultrafilter (Amicon Ultra-4 10 k; 5,000×g 20 min×4 times with PBS) to remove by-products of the chemical reaction and excessive SPDP. Purified pyridyldithiol-activated Pvs25H-A (solution volume, 200 μl) was combined with 1 mg of a reduced COMP-Z (240 μl), and incubated at room temperature overnight. Amicon Ultra-4 10 k (5,000×g 20 min×4 times) was used to remove a by-product (pyridine 2-thione) of the chemical reaction, and the buffer was exchanged to a PBS to obtain a fusion protein COMP-Z/Pvs25H-A.

(Quantification of Binding Partner Molecule)

The concentration of the vaccine fusion delivery vehicle was assayed by the BCA. 100 μg (per COMP-Z) of the vaccine fusion delivery vehicle obtained and 100 μg of COMP-Z obtained in Example 1 as a control were diluted to 300 μl in total, each of which was reacted with 200 μl of an IgG Sepharose (equilibrated with TST, 50% slurry) and adsorption was accomplished using a rotator for 2 hours at 4° C. Centrifugation (600×g 2 min) was carried out to recover a supernatant (500 μl). Subsequently, 1000 μl of TST was used for washing, followed by centrifugation (600×g 2 min), followed by recovery of the wash fractions 1. Furthermore, 200 μl of a 0.5 M ammonium acetate solution (pH 5.5) was used for washing, followed by centrifugation (600×g 2 min), followed by recovery of the wash fractions 2. Finally, 100 μl of a 0.5 M acetic acid solution (pH 3.5) was used to form a dispersion, which was mixed for 10 minutes, followed by centrifugation (600×g 2 min), followed by recovery of 100 μl. From the amount of the protein recovered which was calculated by the BCA assay, the amount of the non-binding molecule was calculated, whereby finally calculating the amount of the binding molecule.

Thus, assuming that the protein present in the supernatant and the wash fractions was a free partner molecule (vaccine antigen), a proportion of binding partner molecule was calculated inversely from the amount of the protein applied. The amount of the protein applied initially was 115.7 μg, which consisted of 85.5698 μg as Pvs25H-A and 30.1302 μg as COMP-Z on the proportion basis. Thus, out of 85.35698 μg of Pvs25H-A, 48.82326 μg corresponded to the non-binding amount (amount of the protein in the supernatant and the wash fractions), resulting in 36.53338 μg as the binding amount. When calculating on the molar basis, 1773.3 pmol of Pvs25H-A was bound. Since 30.1 μg of COMP-Z corresponds to 415.17 pmol, the molar ratio can be indicated as Pvs25H-A:COMP-Z=4.3:1. Consequently, it was shown that a fusion complex in which 4.3 molecules of Pvs25H-A was bound to 1 molecule of COMP-Z was formed.

(Verification of COMP-Z/Pvs25H-A Fusion)

Utilizing the characteristics that COMP-Z binds to an Fc region of an immunoglobulin, a Pvs25H-A specific ELISA method was employed to verify that Pvs25H-A was bound physically to a COMP-Z molecule. First, onto each well of a SUMILON 96-well ELISA plate type S, each 50 μl of Human IgG (hIgG) as a capture antibody was applied at a concentration of 5 μg/ml and allowed to react a whole day and night at 4° C. whereby accomplishing coating. To the hIgG-coated ELISA plate, 150 μl/well of a 1% solution of BSA in PBS was added and allowed to react for 2 hours at 37° C. whereby accomplishing a blocking reaction. After blocking, each applied sample was combined at a concentration of 2 μg/well per COMP-Z with COMP-Z or COMP-Z/Pvs25H-A fusion molecule, and allowed to react for 2 hours at 37° C. This reaction resulted in a capture of the both constructs by means of Fc/Z binding. Also for the purpose of masking a "free" Z domain which escaped from binding with the capture antibody (hIgG), each 50 μl of an excessive amount of hIgG (5 μg/ml) was applied to each well and allowed to react for 2 hours at 37° C. Thereafter, 50 μl/well of an anti-Pvs25 mouse IgG antiserum as a primary antigen (200-fold dilution) was applied and allowed to react for 2 hours at 37° C. Consecutively, 50 μl/well of an AP-conjugated anti-mouse antibody as a secondary antigen (3000-fold dilution) was applied and allowed to react for 2 hours at 37° C. Finally, an AP substrate (Bio-Rad) was used to react at 37° C., and $OD_{415\,nm}$ was measured after appropriate reaction times (5 min, 10 min, 20 min) whereby detecting Pvs25H-A antigen specific signals, which revealed a difference in signals between COMP-Z and COMP-Z/Pvs25H-A, based on which the binding between COMP-Z and Pvs25H-A was proven directly.

Example 3

Immunogenicity Verification Test

30 μg of Pvs25H-A (S) was administered 3 times (0, 2nd and 4th week) to a 7-week old female Balb/c mouse (Nippon SLC) subcutaneously (s.c.), intraperitoneally (i.p.), intravenously (i.v.), and intranasally (i.n.) (n=7, except for the intravenous administration group where n=2). Similarly, a sample (M) which was a mixture of 30 μg of Pvs25H-A and 10.6 μg of COMP-Z, and 40.6 μg of COMP-Z/Pvs25H-A (L) obtained in Example 2 were administered. In addition, 1 μg of a cholera toxin (CT:LBL) and Samples S, L and M adjusted to 30 μg per Pvs25H-A were given intranasally (i.n./CT). Moreover, a mixture of Freund's adjuvant (IFA) in a volume equal to the volume of antigen administered (which is herein 100 μl) and 30 μg of Sample S was given subcutaneously. Furthermore, in the absence of IFA, S, M and L adjusted to 30 μg per Pvs25H-A were given subcutaneously. In the 1st, 3rd and 5th week, a partial blood collection was made to verify an increase in the antibody titer against Pvs25H-A in the 5th week, and then the final blood collection was made in the 6th week. Analysis of the antibody titer was conducted by an ELISA method. Using the serum of the 6th week as being 50-fold diluted and Pvs25H-A as a coat antigen (5 μg/ml), together with a 50-fold diluted serum and a 3000-fold diluted AP conjugated anti-mouse antibody, $OD_{415\,nm}$ was measured employing an AP substrate. As a negative control, the serum obtained in a non-immunized animal group was employed. The results are shown in FIG. 1.

Based on these results, a novel vaccine fusion complex produced here exhibited a response, in the absence of IFA, which is not less than the antibody titer observed in the antigen-only group in the presence of IFA which reflects an ordinary vaccine effect. In other words, it can be assumed that this novel vaccine fusion complex can induce the antibody production predominantly in the absence of an existing adjuvant in a subcutaneous immunity, and the antibody binding domain which was a ligand employed here interacts with an immunoglobulin present on the surface of a B cell whereby inducing the antibody production response.

Example 4

Transmission Blocking Analysis

Figure 2:
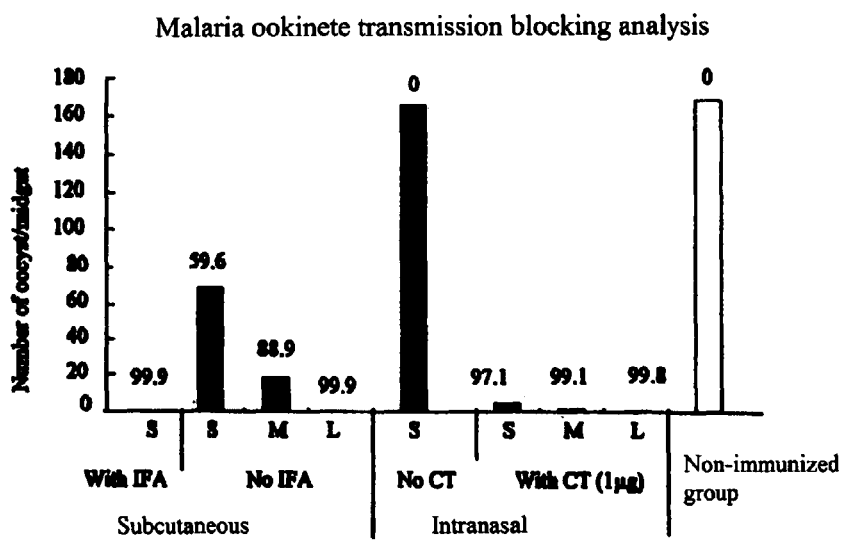
FIG. 2 shows the results of a malaria ookinete transmission blocking analysis in Example 4.

The serum obtained in Example 3 was mixed with each other among the groups (s.c./IFA S, s.c.S, s.c.M, s.c.L, i.n.S, i.n./CT S, i.n./CT M, i.n./CT L), and a mixed serum was used as a sample. An assay was conducted using the blood (*Plasmodium-vivax* gametocyte) taken from four patients. 180 μl of the patient's blood was combined with 180 μl as a mixture of 90 μl of a mixed serum and 90 μl of a normal human serum, and placed in a membrane feeder where it was subjected to a hematophagia by a mosquito (*Anopheles dirus*). The number of oocysts formed in the mesenteron of the mosquito was measured by a microscopic observation. The results are shown in FIG. 2.

Based on these results, the novel malaria vaccine fusion molecule produced here was proven to have an ability of killing an actual *Plasmodium vivax* completely in a group of a predominant increase in the antibody formation. Also based on greater increases in the killing ability in the order of S, M and L, the antibody induced by the molecule produced here was proven to have an ability of recognizing an actual *Plasmodium*, whose efficacy was further increased by adding a ligand. Also since a certain degree of the effect was observed in the M mixture group, it was suggested that the COMP-Z molecule produced itself had an adjuvant activity.

Example 5

Cell Targeting Function Analysis

Figure 3:
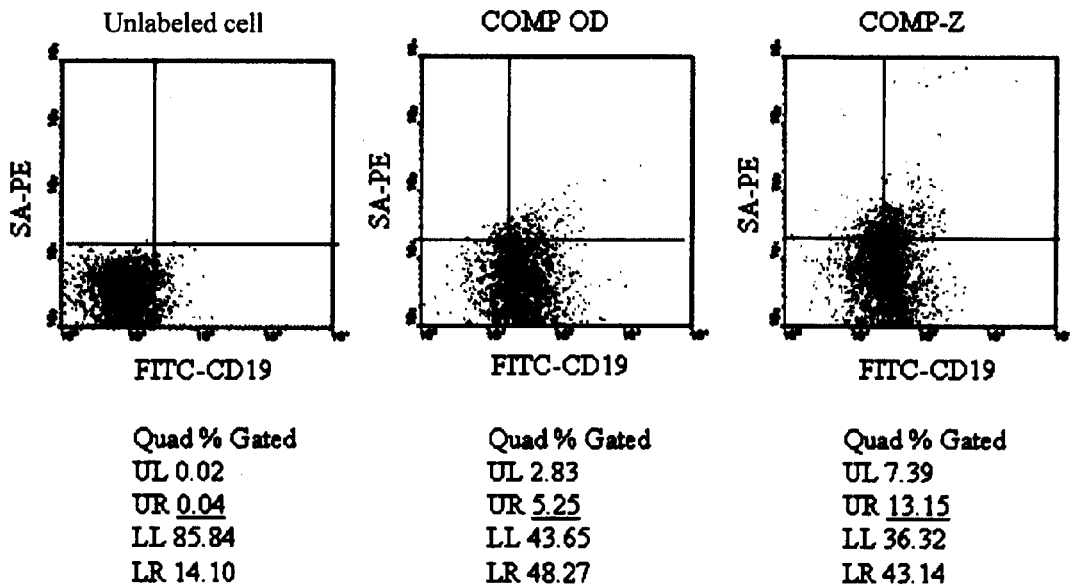
FIG. 3 shows the results of targeting to B cells in Example 5.
Figure 4:
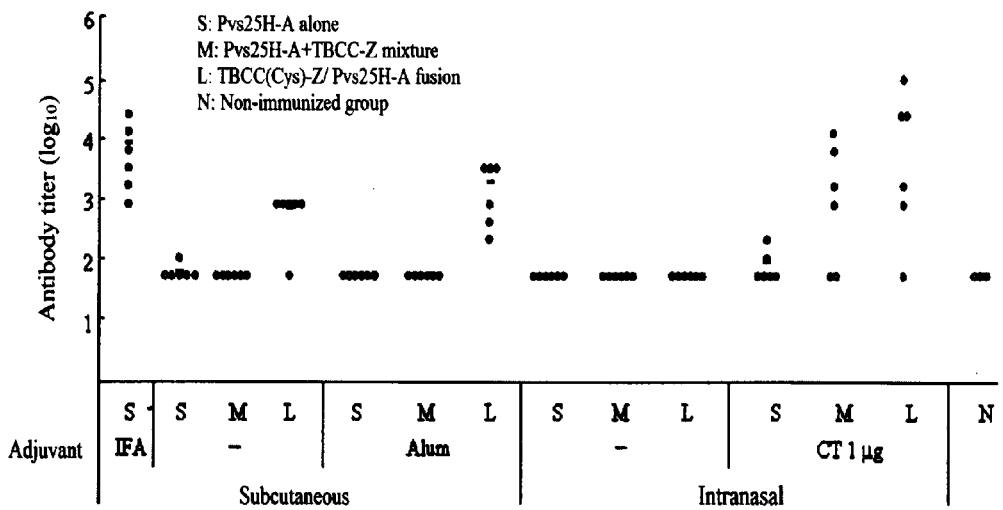
FIG. 4 shows the ELISA data in Example 8.
Figure 5:
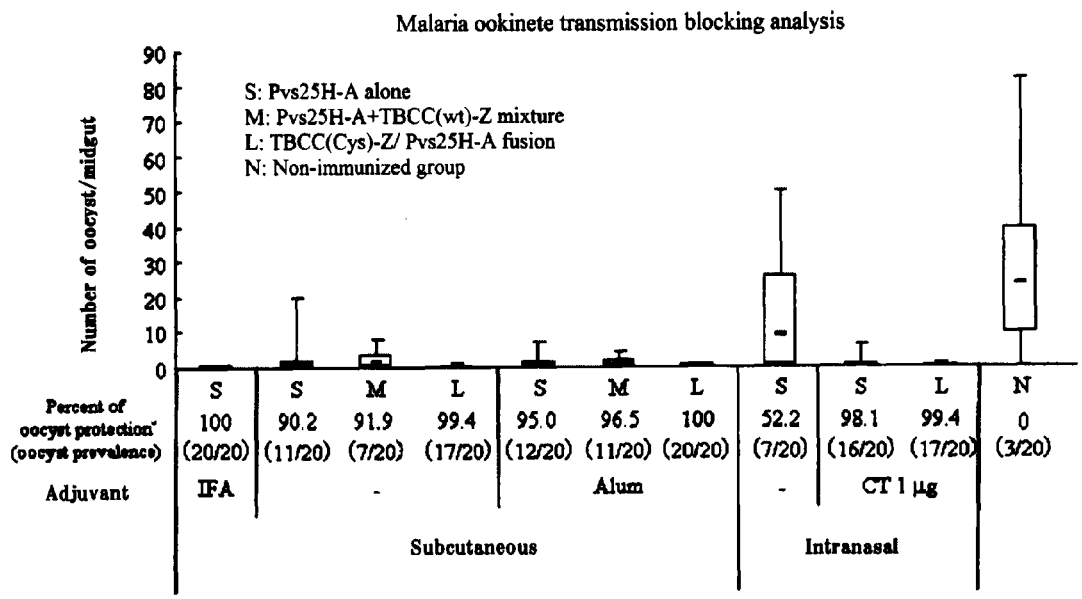
FIG. 5 shows the results of a malaria ookinete transmission blocking analysis in Example 9.

The cell targeting function of COMP-Z obtained in Example 1 was analyzed by a flow cytometric procedure. Thus, a spleen was taken out of a 7-week old Balb/c mouse and used to prepare a splenocyte preparation. Using $10^5$ cells of the splenocyte thus obtained, the detection was conducted with a labeled B cell marker and a labeled COMP-Z, whereby examining the targeting function. As a B cell marker, an FITC-labeled anti-CD19 antibody was employed at a concentration of 0.2 mg/ml. COMP-Z was biotinylated with a maleimide-PE02-biotin, and PE-streptavidin (SA-PE) was further employed at a concentration of 0.0001 mg/ml to conduct the detection. More typically, 0.01 mg of the biotinylated COMP-Z was mixed with a splenocyte prepared at $10^5$ cells/ 100 ml as a suspension in a 1% BSA in PBS, and allowed to react for 30 minutes in ice. Then, hIgG as a masking agent was added at a concentration of 50 mg/ml and allowed to react for 30 minutes at 4° C. Furthermore, a hamster immunoglobulin as an Fc receptor inhibitor was added and allowed to react for 30 minutes at 4° C. Thereafter, centrifugation (1,500 rpm, 5 min) was conducted to discard the supernatant, and a suspension was made in 100 ml of 1% BSA in PBS. Then, the FITC-anti-CD19 antibody and SA-PE were added and allowed to react for 30 minutes at 4° C. Thereafter, centrifugation (1,500 rpm, 5 min) was conducted to discard the supernatant, and a suspension was made in 100 ml of 1% BSA in PBS. Then, centrifugation (1,500 rpm, 5 min) was conducted again to discard the supernatant, and finally a suspension was made in 1% formaldehyde and used as a sample for the flow cytometry. As a sample having no ligands, COMP OD was employed simultaneously to serve as a negative control. The flow cytometry analysis was conducted in accordance with the instruction of FACS system by BD. The results are shown in FIG. 3.

From this analysis, COMP OD exhibited an UR, which indicates the binding of a B cell with a protein, of 5.25%, while COMP-Z exhibited a UR which was increased to 13.15%, which indicated the binding of COMP-Z with the B cell.

Example 6

Production of a TBCC-Z Delivery Vehicle (Cloning of TBCC(wt)-Flexible Linker)

A fusion complex was produced using TBCC as a core molecule. TBCC was designated as TBCC(wt) when using a wild type sequence (SEQ ID NO:34).

While the flexible linker was introduced after cloning of COMP when producing COMP-Z, here in the case of TBCC the cloning was conducted simultaneously for convenience. In a typical introduction method, TBCC(wt)-flexible linker was cloned first. Thus, in order to obtain a 79 amino acid residue of TBCC(wt)-flexible linker (SEQ ID NO:24), a sense primer SEQ ID NO:25 and an antisense primer SEQ ID NO:26 were produced, annealed and then introduced into a pCR2.1 vector, whereby accomplishing a subcloning.

After digestion with restriction enzymes NcoI and XhoI, followed by subcloning into an *E. coli* expression vector pET-21d at the NcoI-XhoI site, followed by an ordinary calcium phosphate method to transform into an *E. coli* DH5 alpha. Then a screening on the basis of ampicillin as a drug resistance marker present in the vector was conducted to select an intended gene-transduced clone. This clone was further transformed into a protein-expressing *E. coli* strain BL21 (DE3) by a calcium phosphate method, followed by screening with ampicillin, followed by construction of a TBCC(wt)-flexible linker-expressing construct. This expression strain was pre-cultured one whole day and night at 37° C. in 100 ml of an ordinary LB-Amp medium, and then inoculated at $OD_{600\,nm}$=0.1 to four tubes each containing 250 ml of the LB-Amp medium, which were cultured for 1.5 hours at 37° C. At this time point, the turbidity $OD_{600\,nm}$ was measured to ensure an $OD_{600\,nm}$ of 0.4 to 0.6, and then isopropyl-β-thiogalactopyranoside (IPTG) was added at a final concentration of 1 mM, and a whole day and night culture at 37° C. was conducted to induce the expression of the protein. After inducing the expression, the culture supernatant was separated by centrifugation followed by filtration through a 0.45 μm filter, followed by purification by an affinity chromatography on a His-tag column, followed by a 15% acrylamide gel SDS-PAGE of an aliquot of the purified protein, whereby verifying the expression of the TBCC(wt)-flexible linker moiety.

(Fusion of Ligand Moiety)

The above-mentioned TBCC(wt)-flexible linker was subjected to the following method to construct a ligand moiety. As a ligand, an antibody binding domain (Z domain) which is a B domain homolog derived from a *Staphylococcus aureus*-derived Protein A (SpA) was employed (SEQ ID NO:7). This Z domain was fused to the C terminal of the TBCC(wt)-flexible linker constructed previously in a gene engineering manner. Typically, a synthetic oligo of a sense primer SEQ ID NO:21 and an antisense primer SEQ ID NO:22 was produced, annealed and then introduced into a pCR2.1 vector, whereby completing the cloning of the Z domain. After verifying the base sequence followed by digestion with restriction enzymes SalI and XhoI, subcloning into the XhoI site of the pET-21d-TBCC(wt)-flexible linker was conducted, whereby completing the construction (pET-21d-TBCC(wt)-Z).
(Production of Cys Residue-Carrying Construct TBCC (Cys)-Z)

While TBCC(wt)-Z (SEQ ID NO:27) can be bound in a gene engineering manner with a vaccine antigen and the like, it does not have a cysteine residue utilized in chemical fusion, and accordingly cysteine residue-carrying constructs TBCC (S52C)-Z (SEQ ID NO:28) and TBCC(C60)-Z (SEQ ID NO:29) were produced. TBCC(S52C)-Z is a construct in which the 52nd serine residue in TBCC(wt)-Z was replaced with a cysteine residue. TBCC(C60)-Z is a construct in which a cysteine residue was inserted to the 60th amino acid of TBCC(wt)-Z. Introduction of Cys was performed using QuickChange Site-Directed Mutagenesis Kit (Stratagene). Typically, using TBCC(wt)-Z as a template, a sense primer SEQ ID NO:30 and an antisense primer SEQ ID NO:31 for TBCC(S52C)-Z and using TBCC(wt)-Z as a template, a sense primer SEQ ID NO:32 and an antisense primer SEQ ID NO:33 for TBCC(C60)-Z, a PCR method was conducted to amplify intended products. Each PCR amplification product obtained was combined with 1 µl of DpnI and incubated for 1 hour at 37° C., and then transformed into an *E. coli* XL1-Blue strain. Screening with an LB-Amp medium was conducted and the resultant respective clones were constructed, whereby verifying the base sequences. Thereafter, transformation into an *E. coli* BL21(DE3) strain was conducted respectively.
(Methods of Culture, Expression Induction and Purification of Various TBCC-Z (Wild Type and Cys-Carrying Type) Protein)

10 µl of a frozen stock of an *E. coli* strain BL21 (DE3) containing pET-21d-TBCC-Z was inoculated to 100 ml of an LB-Amp medium, which was cultured a whole night at 37° C. Subsequently, inoculation was conducted at $OD_{600\ nm}$=0.1 to four tubes each containing 250 ml of the LB-Amp medium, which were cultured for 1.5 hours at 37° C. At this time point, the turbidity $OD_{600\ nm}$ was measured to ensure an $OD_{600\ nm}$ of 0.4 to 0.6, and then isopropyl-β-thiogalactopyranoside (IPTG) was added at a final concentration of 1 mM, and a whole day and night culture at 37° C. was conducted to induce the expression of the protein. After inducing the expression, all cultures were combined and subjected to a centrifugation (8,000 rpm, 20 min, 4° C., 2 times) to separate into the cells and the culture supernatant. An aliquot of the culture supernatant was recovered for an expression analysis.

The culture supernatant was combined with imidazole at a final concentration of 20 mM, filtered through a 0.45 µm filter, and prepared for applying to a chromatography. To 5 ml of HisTrap column (GE Healthcare), a washing buffer (20 mM imidazole, 20 mM phosphate buffer, pH7.4) was applied for column equilibration in a volume 5 times the column volume. To the column thus equilibrated, the prepared samples were applied using a peristaltic pump, whereby conducting an affinity chromatography.

After applying the sample, the column was then washed and eluted. Washing was conducted using a 5-column volume of a washing buffer followed by elution with a 5-column volume of an elution buffer (500 mM imidazole, 20 mM phosphate buffer, pH7.4). The culture supernatant, the flow-through fraction, the wash fraction, and the elution fraction were analyzed by a 15% acrylamide gel SDS-PAGE. After running, the expression pattern was examined to ensure the expression in the elution fraction, followed by concentration using an ultrafiltration membrane (Amicon Ultra-15 30 kDa), followed by replacement with PBS. Then, for obtaining a higher purity, a concentrated TBCC-Z solution was combined with DTT at a final concentration of 50 mM and shaken at room temperature for 30 minutes, subjected to a 10-fold dilution with PBS (final DTT concentration of 5 mM), and then applied again to the HisTrap column (5 ml). Then, a 5-column volume of the washing buffer was applied and then a 5-column volume of the elution buffer was used for elution. The pre-column treatment sample, the flow-through fraction, the wash fraction, and the elution fraction were analyzed by a 15% acrylamide gel SDS-PAGE. After running, the expression pattern was examined to ensure the expression in the elution fraction, followed by concentration using an ultrafiltration membrane (Amicon Ultra-15 30 kDa), followed by replacement with PBS. Using a BCA Protein Assay Reagent (bicinchoninic acid) (PIERCE) was employed for quantification of the protein, and the results indicated that the concentrations of the TBCC-Z protein were 3.1 mg for TBCC(wt)-Z, 14.5 mg for TBCC(S52C)-Z, and 10.2 mg for TBCC(C60)-Z. TBCC(S52C)-Z and TBCC(C60)-Z were designated collectively as TBCC(Cys)-Z.
(Endotoxin Removal Treatment of Various TBCC-Z)

Since an endotoxin was suspected to be contaminating a recombinant protein produced with an *E. coli*, the endotoxin was removed and the endotoxin concentration in the protein solution was assayed prior to conducting an immune experiment.

Since the endotoxin was as small as about 10 kDa while TBCC-Z has a molecular weight of about 60 kDa, a treatment was conducted using a 50 kDa dialysis membrane. The exterior solution employed was a PBS, which was exchanged every several hours at 4° C. over a finally whole day and night dialysis. A sample thus dialyzed was applied onto an endotoxin removal column (PIERCE; Detoxi-Gel Endotoxin Removal Gel) where the endotoxin was removed. A sample after passing the endotoxin removal column was subjected to a BCA quantification and a limulus test (LAL) was conducted to assay the endotoxin concentration. Thus, using a LAL Pyrogen Single Test for 25 cycles, a sample diluted to a final volume of 0.25 ml was assayed. The sample was diluted with an endotoxin-free water. A sample solution adjusted at a required concentration was injected into a vial using a syringe, mixed gently, placed in a box or equivalent for avoiding fall down, where it was allowed to react for 1 hour at 37° C. After 1 hour, the vial was taken out while avoiding vibration, and inverted once. The judgment was endotoxin positive when the sample solution was solidified while endotoxin negative when the solution was not solidified or partly dropped down as being dissolved. Since the endpoint is defined as the level just before the dilution level at which the judgment becomes negative, from which the number of the endotoxin units was calculated, and when a level of 500 pg endotoxin/µg of protein or higher was observed then the sample was applied again to the endotoxin removal column, and the same procedure was repeated until a level of 500 pg endotoxin/µg of protein or lower was observed.

Example 7

Production of Vaccine Delivery Vehicle Fusion Complex (2)

Pvs25 which is a transmission blocking antigen of the *Plasmodium vivax* was fused with TBCC(Cys)-Z chemically utilizing an SH group present in TBCC(Cys)-Z. The vaccine antigen Pvs25 employed was a Pvs25H A form (Pvs25H-A) having a uniform conformation expressed in a yeast *Pichia pastoris*. As a crosslinker required for the fusion, an SPDP was employed and the following reaction schemes were employed to establish a fusion complex TBCC-Z/Pvs25H-A.

The fusion was conducted using a TBCC-Z tetramer (2 mg; 1.55 ml; 34 nmol), Pvs25H-A (2.8 mg; 1.46 ml; 137.2 nmol).

(Reducing Treatment)

First, a reducing treatment was conducted for ensuring an SH group in a reduced form in TBCC(Cys)-Z. While TBCC (Cys)-Z has an SH group in a reduced form even when being expressed in an *E. coli*, the reducing treatment was conducted for the purpose of increasing the number of available SH groups. A TBCC(Cys)-Z (4 mg) solution was combined with DTT at a final concentration of 50 mM, and shaken for 30 minutes at room temperature. Thereafter, DTT was removed by an ultrafilter (Amicon Ultra-4 10K; 5,000×g 20 min×4 times with PBS), and the protein concentration was determined using a BCA assay method.

(Fusion Treatment)

Immediately before use, 2 mg of an SPDP was dissolved in 320 μl of DMSO to prepare a 20 mM SPDP solution. 84 μl of the 20 mM SPDP solution was combined with 5.6 mg/2.8 ml of Pvs25H-A, and incubated at room temperature for 60 minutes (production of pyridyldithiol-activated Pvs25H-A). Purification was conducted using an ultrafilter (Amicon Ultra-4 10 k; 5,000×g 20 min×4 times with PBS) to remove by-products of the chemical reaction and excessive SPDP. Purified pyridyldithiol-activated Pvs25H-A (2.8 mg/1.46 ml) was combined with 2 mg of reduced TBCC(Cys)-Z (1550 μl), and incubated at room temperature overnight. Amicon Ultra-4 10 k (5,000×g 20 min×4 times) was used to remove a by-product (pyridine 2-thione) of the chemical reaction, and the buffer was exchanged to a PBS to obtain a fusion protein TBCC(Cys)-Z/Pvs25H-A.

(Verification of TBCC-Z/Pvs25H-A Fusion)

Utilizing the characteristics that TBCC-Z binds to an Fc region of an immunoglobulin, a Pvs25H-A specific ELISA method was employed to verify that Pvs25H-A was bound physically to a TBCC(Cys)-Z molecule. First, onto each well of a SUMILON 96-well ELISA plate type S, each 50 μl of Human IgG (hIgG) as a capture antibody was applied using a bicarbonate buffer at a concentration of 5 μg/ml and allowed to react a whole day and night at 4° C. whereby accomplishing coating. To the hIgG-coated ELISA plate, 150 μl/well of a 1% solution of BSA in PBS was added and allowed to react for 2 hours at 37° C. whereby accomplishing a blocking reaction. After blocking, each sample was combined at a concentration of 2 μg/well per TBCC(Cys)-Z with TBCC (Cys)-Z or TBCC(Cys)-Z/Pvs25H-A fusion molecule, and allowed to react for 2 hours at 37° C. This reaction resulted in a capture of the both constructs by means of Fc/Z binding. Also for the purpose of masking a "free" Z domain which escaped from binding with the capture antibody (hIgG), each 50 μl of an excessive amount of hIgG (5 μg/ml) was applied to each well and allowed to react for 2 hours at 37° C. Thereafter, 50 μl/well of an anti-Pvs25 mouse IgG antiserum as a primary antigen (200-fold dilution) was applied and allowed to react for 2 hours at 37° C. Consecutively, 50 μl/well of an AP-conjugated anti-mouse antibody as a secondary antigen (3000-fold dilution) was applied and allowed to react for 2 hours at 37° C. Finally, an AP substrate (Bio-Rad) was used to react at 37° C., and $OD_{415\ nm}$ was measured after appropriate reaction times (5 min, 10 min, 20 min) whereby detecting Pvs25H-A antigen specific signals, which revealed a difference in signals between TBCC(Cys)-Z and TBCC(Cys)-Z/Pvs25H-A, based on which the binding between TBCC (Cys)-Z and Pvs25H-A was proven directly.

Example 8

Immunogenicity Verification Test

30 μg of Pvs25H-A (S) was administered 3 times (0, 2nd and 4th week) to a 7-week old female Balb/c mouse (Nippon SLC) subcutaneously (s.c.) and intranasally (i.n.) (n=7). Similarly, a sample (M) which was a mixture of 30 μg of Pvs25H-A and 21.4 μg of TBCC(S52C)-Z or 21.4 μg of TBCC(C60)-Z, or 51.4 μg of TBCC(S52C)-Z/Pvs25H-A (L) or TBCC(C60)-Z/Pvs25H-A (L) obtained in Example 6 were administered. In addition, 1 μg of a cholera toxin (CT:LBL) was combined with Samples S, M and L, and given intranasally (i.n./CT). Moreover, a mixture of incomplete Freund's adjuvant (IFA) or an Alum adjuvant in a volume equal to the volume of antigen administered (which is herein 100 μl) and 30 μg of Sample S was given subcutaneously (s.c./IFA, s.c./Alum).

Furthermore, in the absence of IFA, S, M and L adjusted to 30 μg per Pvs25H-A were given subcutaneously. In the 1st, 3rd and 5th week, a partial blood collection was made to verify an increase in the antibody titer against Pvs25H-A in the 5th week, and then the final blood collection was made in the 6th week. Analysis of the antibody titer was conducted by an ELISA method. Using the serum of the 6th week as being 50-fold diluted and Pvs25H-A as a coat antigen (5 μg/ml), together with a 50-fold diluted serum and a 4000-fold diluted anti-mouse IgG-AP, $OD_{415\ nm}$ was measured employing an AP substrate. As a negative control, the serum obtained in a non-immunized animal group was employed. The results are shown in FIG. 4.

Based on these results, a novel vaccine fusion complex produced here can induce a response which is equivalent to the antibody titer observed in the antigen-only group in the presence of IFA which reflects an ordinary vaccine effect, and the mixed administration with the Alum adjuvant resulted in a further enhancement. In other words, it was revealed that while this novel vaccine fusion complex can induce the antibody response independently of an adjuvant in a subcutaneous immunity, it can induce a more effective antibody production when used concomitantly with a clinically employed adjuvant.

Example 9

Transmission Blocking Analysis

The serum obtained in Example 8 was mixed with each other among the groups (s.c./IFA S, s.c.S, s.c.M, s.c.L, s.c./Alum S, s.c./Alum M, s.c./Alum L, i.n.S, i.n./CT S, i.n./CT L), and a mixed serum was used as a sample. An assay was conducted using the blood (*Plasmodium-vivax* gametocyte) taken from four patients. 180 μl of the patient's blood was combined with 180 μl as a mixture of 90 μl of a mixed serum and 90 μl of a normal human serum, and placed in a membrane feeder where it was subjected to a hematophagia by a mosquito (*Anopheles dirus*). The number of oocysts formed in the mesenteron of the mosquito was measured by a microscopic observation. The results are shown in FIG. 5.

Based on these results, the novel malaria vaccine fusion molecule produced here which used TBCC as a core was proven to have an ability of killing an actual *Plasmodium vivax* completely in a group of a predominant increase in the antibody formation. In addition to the greater increases in the killing ability in the order of S, M and L, an increased killing ability when used concomitantly with Alum was revealed, suggesting a possibility of enhancing the effect of an existing adjuvant.

Example 10

Production of Vaccine Delivery Vehicle Fusion Complex (3)

A fusion complex carrying MSP1-19 was produced and its antibody response function was examined. While MSP1-19 is a malaria antigen similarly to Pvs25, it is a merozoite phase antigen, and the transmission blocking antigen Pvs25 is expressed by a malaria ookinete in a mosquito, while MSP1-19 is an antigen expressed by a malaria ookinete in a mammal.

Typically, MSP1-19 was fused via a chemical bond utilizing an SH group present inside of TBCC(Cys)-Z and COMP-Z. The vaccine antigen MSP1-19 employed was a MSP1-19H S form (MSP1-19H-S) having a uniform conformation expressed in a yeast *Pichia pastoris*. As a crosslinker required for the fusion, an SPDP was employed and the following reaction schemes were employed to establish a fusion complex TBCC(Cys)-Z/MSP1-19H-S and COMP-Z/MSP1-19H-S.

The fusion was conducted using a TBCC-Z tetramer (750 μg: 625 μl: 12.5 nmol), COMP-Z pentamer (750 μg: 625 μl: 10.4 nmol), and MSP1-19H-S (3 mg: 1.5 ml: 210 nmol).

(Reducing Treatment)

First, a reducing treatment was conducted for ensuring an SH group in a reduced form in TBCC(Cys)-Z and COMP-Z. While TBCC(Cys)-Z and COMP-Z has an SH group in a reduced form even when being expressed in an *E. coli*, the reducing treatment was conducted for the purpose of increasing the number of available SH groups. A TBCC(Cys)-Z and COMP-Z (4 mg) solution was combined with DTT at a final concentration of 50 mM, and shaken for 30 minutes at room temperature. Thereafter, DTT was removed by an ultrafilter (Amicon Ultra-4 10K; 5,000×g 20 min×4 times with PBS), and the protein concentration was determined using a BCA assay method.

(Fusion Treatment)

Immediately before use, 2 mg of an SPDP was dissolved in 320 μl of DMSO to prepare a 20 mM SPDP solution. 84 μl of the 20 mM SPDP solution was combined with 3 mg/1.5 ml of MSP1-19H-S, and incubated at room temperature for 60 minutes (production of pyridyldithiol-activated MSP1-19H-S). Purification was conducted using an ultrafilter (Amicon Ultra-4 10 k; 5,000×g 20 min×4 times with PBS) to remove by-products of the chemical reaction and excessive SPDP. Purified pyridyldithiol-activated MSP1-19H-S (3 mg/1.5 ml) was combined with 0.5 mg of reduced TBCC(Cys)-Z and COMP-Z (500 μl), and incubated at room temperature overnight. Amicon Ultra-4 10 k (5,000×g 20 min×4 times) was used to remove a by-product (pyridine 2-thione) of the chemical reaction, and the buffer was exchanged to a PBS to obtain a fusion proteins TBCC(Cys)-Z/MSP1-19H-S and COMP-Z/MSP1-19H-S.

(Verification of TBCC(Cys)-Z and COMP-Z Fusion)

Utilizing the characteristics that TBCC-Z binds to an Fc region of an immunoglobulin, a MSP1-19H-S specific ELISA method was employed to verify that MSP1-19H-S was bound physically to a TBCC(Cys)-Z and COMP-Z molecules. First, onto each well of a SUMILON 96-well ELISA plate type S, each 50 μl of Human IgG (hIgG) as a capture antibody was applied using a bicarbonate buffer at a concentration of 5 μg/ml and allowed to react a whole night at 4° C. whereby accomplishing coating. To the hIgG-coated ELISA plate, 150 μl/well of a 1% solution of BSA in PBS was added and allowed to react for 2 hours at 37° C. whereby accomplishing a blocking reaction. After blocking, each sample was combined at a concentration of 2 μg/well per TBCC(Cys)-Z and COMP-Z molecules with TBCC-Z/MSP1-19H-S and COMP-Z/MSP1-19H-S fusion molecule, and allowed to react for 2 hours at 37° C. This reaction resulted in a capture of the both constructs by means of Fc/Z binding. Also for the purpose of masking a "free" Z domain which escaped from binding with the capture antibody (hIgG), each 50 μl of an excessive amount of hIgG (5 μg/ml) was applied to each well and allowed to react for 2 hours at 37° C. Thereafter, 50 μl/well of an anti-MSP1-19 mouse IgG antiserum as a primary antigen (200-fold dilution) was applied and allowed to react for 2 hours at 37° C. Consecutively, 50 μl/well of an AP-conjugated anti-mouse antibody as a secondary antigen (3000-fold dilution) was applied and allowed to react for 2 hours at 37° C. Finally, an AP substrate (Bio-Rad) was used to react at 37° C., and $OD_{415\ nm}$ was measured after appropriate reaction times (5 min, 10 min, 20 min) whereby detecting MSP1-19H-S antigen specific signals, which revealed a difference in signals between TBCC(Cys)-Z and COMP-Z and TBCC(Cys)-Z/MSP1-19H-S and COMP-Z/MSP1-19H-S, based on which the binding of TBCC(Cys)-Z and COMP-Z with MSP1-19H-S was proven directly.

Example 11

Immunogenicity Verification Test

Figure 6:
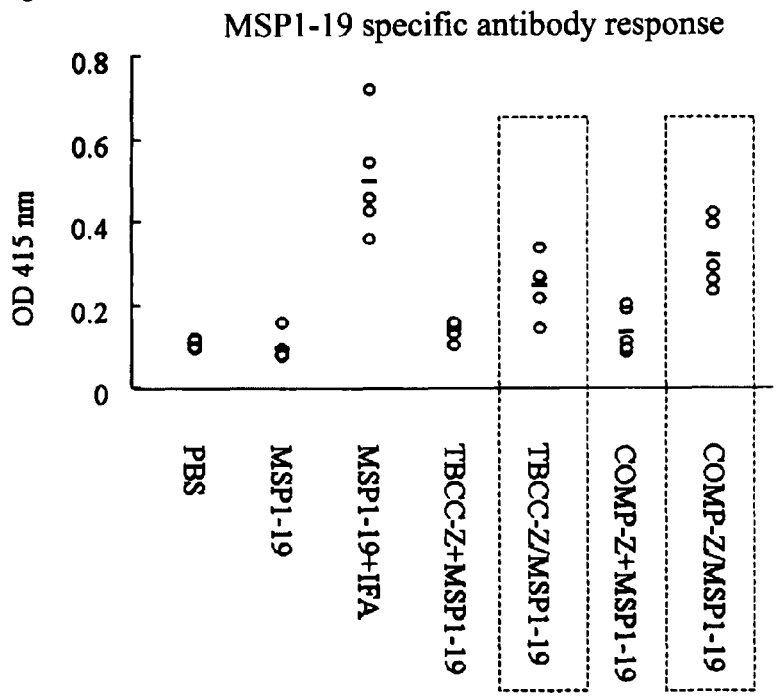
FIG. 6 shows the responses by antibodies to an antigen in the malaria merozoite phase in Example 11.

30 μg of MSP1-19H-S (S) was administered 3 times (0, 2nd and 4th week) to a 7-week old female C57B/6 mouse (Nippon SLC) subcutaneously (s.c.). Similarly, a sample (M) which was a mixture of 30 μg of MSP1-19H-S and 10.6 g of TBCC (Cys)-Z or COMP-Z, or 40.6 μg of TBCC(Cys)-Z/MSP1-19H-S and COMP-Z/MSP1-19H-S (L) obtained in Example 10 were administered. Moreover, a mixture of Freund's adjuvant (IFA) in a volume equal to the volume of antigen administered (which is herein 100 μl) and 30 μg of Sample S was given subcutaneously. In the 1st, 3rd and 5th week, a partial blood collection was made to verify an increase in the antibody titer against MSP1-19H-S in the 5th week, and then the analysis of the antibody titer was conducted in the 6th week. The analysis of the antibody titer was conducted by an ELISA method. Using the serum of the 6th week as being 50-fold diluted and MSP1-19H-S as a coat antigen (5 μg/ml), together with a 50-fold diluted serum and a 3000-fold diluted AP conjugated anti-mouse antibody, $OD_{415\ nm}$ was measured employing an AP substrate. As a negative control, the serum obtained in a non-immunized animal group was employed. The results are shown in FIG. 6.

Based on these results, a novel malaria vaccine fusion complex produced here whose antigen was exchanged also exhibited a significantly higher response when compared with the antigen-only group. In other words, it can be assumed that the TIP-carried antigen enhances the immunogenicity regardless of the types. Consequently, the versatility of TIPs was revealed.

INDUSTRIAL APPLICABILITY

Since a drug delivery vehicle according to the present invention has a high flexibility in designing its constituent molecule members, it allows for a high versatility in addition to its excellent safeness, and it is also possible to allow a drug to reach a target cell or tissue efficiently and to enhance the effect of the drug. Accordingly, it is extremely useful as a platform for a drug delivery system against infectious diseases and the like.

The invention claimed is:

1. A vaccine which comprises
  (A) a multimeric fusion protein which contains
    (1) two to five monomeric units of COMP (cartilage oligomeric matrix protein), which are fused to
    (2) at least one antibody binding domain derived from *Staphylococcus* protein A, wherein each unit of the multimeric fusion protein is covalently attached to
  (B) an antigen capable of inducing antibody formation and cellular immunity.

2. The vaccine of claim 1, wherein the COMP (cartilage oligomeric matrix protein) comprises a polypeptide consisting of the amino acid sequence represented by SEQ ID NO: 5 or 6 or an amino acid sequence having at least 95% homology to SEQ ID NO: 5 or 6 and retains a coiled coil structure.

3. The vaccine of claim 1, wherein the antibody binding domain derived from *Staphylococcus* protein A comprises a polypeptide consisting of the amino acid sequence represented by SEQ ID NO: 7 or an amino acid sequence having at least 95% homology to SEQ ID NO:7 and retaining the function of the antibody binding domain derived from *Staphylococcus* protein A.

4. The vaccine of claim 1, comprising a polypeptide consisting of the amino acid sequence represented by SEQ ID NO: 23 or 27 or an amino acid sequence having at least 95% homology to SEQ ID NO: 23 or 27 and retaining the function of SEQ ID NO: 23 or 27.

5. The vaccine of claim 1, wherein the antigen originates from arthropod-mediated diseases or parasitic, bacterial or viral infections.

6. The vaccine of claim 5, wherein the antigen is a Japanese encephalitis virus coat protein or a *Plasmodium* surface protein.

7. An adjuvant which comprises
  (A) a multimeric fusion protein which contains
    (1) two to five monomeric units of COMP (cartilage oligomeric matrix protein), which are fused to
    (2) at least one antibody binding domain derived from *Staphylococcus* protein A, wherein each unit of the multimeric fusion protein is covalently bonded to
  (B) an adjuvant molecule.

8. The adjuvant of claim 7, wherein the COMP (cartilage oligomeric matrix protein) comprises a polypeptide consisting of the amino acid sequence represented by SEQ ID NO: 5 or 6 or an amino acid sequence having at least 95% homology to SEQ ID NO: 5 or 6 and retains a coiled coil structure.

9. The adjuvant of claim 7, wherein the antibody binding domain derived from *Staphylococcus* protein A comprises a polypeptide consisting of the amino acid sequence represented by SEQ ID NO: 7 or an amino acid sequence having at least 95% homology to SEQ ID NO:7 and retaining the function of the antibody binding domain derived from *Staphylococcus* protein A.

10. The adjuvant of claim 7, comprising a polypeptide consisting of the amino acid sequence represented by SEQ ID NO: 23 or 27 or an amino acid sequence having at least 95% homology to SEQ ID NO: 23 or 27 and retaining the function of SEQ ID NO: 23 or 27.

11. The adjuvant of claim 7, wherein the adjuvant molecule is selected from the group consisting of a cholera toxin (CT), a cholera toxin B subunit (CTB), a cholera toxin A subunit (CTA), a *Haemophilus* pertussis toxin (PT), a *Haemophilus* pertussis toxin S1 subunit (PTS1), a Toll-like receptor 9 (TLR9) ligand, a Toll-like receptor 4 (TLR4) ligand and a cationic peptide having a membrane permeating function.

12. A method of inducing an immune response, comprising administering an effective amount of the vaccine of claim 1 to a subject.

13. A method of inducing an immune response, comprising administering an effective amount of the vaccine of claim 7 to a subject.

* * * * *